(12) United States Patent
Schaffer et al.

(10) Patent No.: US 7,560,262 B2
(45) Date of Patent: Jul. 14, 2009

(54) POLYNUCLEOTIDE SEQUENCES ENCODING ALKALINE α-GALACTOSIDASES AND METHODS OF USING SAME

(75) Inventors: Arthur Schaffer, Modi'in (IL); Nir Carmi, Lapid (IL); Marina Petreikov, Rishon LeZion (IL); David Granot, Jerusalem (IL); Yoram Eyal, Masilat Zion (IL)

(73) Assignee: The State of Israel - Ministry of Agriculture & Rural Development, Beit-Dagen (IL)

( * ) Notice: Subject to any disclaimer, the term of this patent is extended or adjusted under 35 U.S.C. 154(b) by 222 days.

(21) Appl. No.: 10/990,156

(22) Filed: Nov. 15, 2004

(65) Prior Publication Data

US 2005/0208520 A1   Sep. 22, 2005

Related U.S. Application Data

(63) Continuation of application No. PCT/IL03/00392, filed on May 15, 2003.

(60) Provisional application No. 60/380,254, filed on May 15, 2002.

(51) Int. Cl.
  *C12N 9/40* (2006.01)
  *C12Q 1/68* (2006.01)
  *C12N 15/00* (2006.01)
  *C12P 21/06* (2006.01)
  *C07H 21/04* (2006.01)

(52) U.S. Cl. .................. 435/208; 435/69.1; 435/320.1; 435/6; 536/23.2

(58) Field of Classification Search ............ 435/4, 435/6, 69.1, 183, 200, 208, 252.3, 320.1; 536/23.2, 23.4, 23.5, 23.7, 23.74
See application file for complete search history.

(56) References Cited

FOREIGN PATENT DOCUMENTS

| WO | WO 0005351 | 2/2000 |
|----|----|----|
| WO | WO 03/097791 | 11/2003 |

OTHER PUBLICATIONS

Guo et al., Protein tolerance to random amino acid change. PNAS., 2004, vol. 101: 9205-9210. Published online Jun. 14, 2004.*
Carmi et al. "Cloning and Functional Expression of Alkaline α-Galactosidase From Melon Fruit: Similarity to Plant SIP Proteins Uncovers A Novel Family of Plant Glycosylhydrolases", The Plant Journal, 33: 97-106, 2003.
Carmi et al. Database GenBank, National Library Of Medicine (Bethesda, MD, USA) No. AY114164, (SEQ ID No. 5), 2003.
Carmi et al. Database GenBank, National Library Of Medicine (Bethesda, MD, USA) No. AY114165, (SEQ ID No. 9), 2003.
R. H Lee. et al., XP002362255, "Oryza Sativa Putative See Imbibition Protein mRNA Partial Cds" Database EMBL [Online] Sequence Version Archive Jan. 22, 2002, Chen SCG:Retrieved from EMBL accession No. AF251068.
Z Gao et al., XP002128580, "A Novel Alkaline Alpha-Galactosidase From Melon Fruit With A Substrate Peference For Raffinose" Plant Physiology, American Society Of Plant Physiologists, vol. 119, No. 3,),pp. 979-987 (1999).
Thomas Peterbauer et al., XP-002361253, "Functional Expression Of A cDNA Encoding Pea (*Pisum sativum L.*) Raffiones Synthase, Partial Purification Of The Enzyme From Maturing Seeds, And Steady-State Kinetic Analysis Of Raffinose Synthesis." Planta. vol. 215, No. 5, pp. 839-846 (2002).
J A. Feurtado et al., XP002361254, "The Cloning And Characterization Of Alpha-Galactosidase Present During And Following Germination Of Tomato (*Lycopersicon esculentum* Mill.) Seed", Journal of Experimental Botany, vol. 52, No. 359, pp. 1239-1249, (2001).

* cited by examiner

*Primary Examiner*—Richard Hutson
*Assistant Examiner*—Ganapathirama Raghu

(57) ABSTRACT

The present invention provides a method of identifying alkaline-α-galactosidases. Also provided are polynucleotide sequences encoding polypeptides having an alkaline-α-galactosidase activity, polynucleotides and oligonucleotide analogs derived from the polynucleotide sequences, peptides and peptide analogues, antibodies recognizing same and methods of using same.

11 Claims, 11 Drawing Sheets

Figure 1a

```
   1 ATGACGGTTGGTGCTGGAATTACTATCTCCGATGCGAATTTGACGGTGTTGGGAAATCGTGTTTATCCGATGTTCATAA
  81 TAACATTACTCTCACGGCGGCCCGGGTGGTGGTGATGAACGGCGCCTTCATAGGAGTTCAATCTGATCAGATCGGTA
 161 GTCGCCGAGTTTTTCCTATTGGGAAATTGATAGGGTTGAGATTCTTGATTGTCTTTCGATTCAAATTATGGTGATGACT
 241 CAAAGAATGGGGTGTTCCGGTCAAGAAGTTCCATTGATACACAATTTCTTGTGGTGGAAACACGTGATGGTTCTAACAT
 321 TGCCCGGAAATGGAGGAAGGCGATGCCGTTTATACTGTTTTTCTTCCTATTCTTGAAGGCGATTTCAGAGCTGTTCTTC
 401 AAGGGAATGATAATAATGAAATTGAAATCTGTTTAGAAACCAAGTGTAGATGGTTTGAGGTAGCCATTTG
 481 GTGTTTGTGGGTGCTGGATCAGATCCTTTGAAACATTACTTATGCAGTCAAGTCTGTTGAAAAGCATTTGCAAACTTT
 561 TGCTCATCGCGAAAGAAAGATGCCTGATATTTTGAACTGGTTCGGCTGGCTGGTGCACATGGATGCTCTTCTACACTGATG
 641 TCACTTCAGATGGCGTCAAGAAGGTCTTGAAAGCTTTGAGAATGGAGAATTCCTCCCAAGTTTGTCATTATCGATGAT
 721 GGATGCCAATCAGTTGCCAAGGATGCTACTAGTGCTGATTGCAAAGCTGATAACACAGCAAACTTTGCAAACAGGTTAAC
 801 TCACATAAAAGAGAATTACAAATTCAAAAGATGGCAAAGAGGGTGAAAGAATTGAGAACCCTGCACTGGGTCTTCAAC
 881 ATATTGTGTCCTACATGAAAGAGAATGCGACCAAGTATGTTTATGTTTGGCATGCCATAACAGGCTACTGGGGTGGT
 961 GTGAGTGCTGGAGTTAAAGAGTGATGCTTTGAATAGCATCACCAAAACTGGACTTGGCCTTGTGAACCCTGAACCCTGGCGAATCAAA
1041 TGAGCCATGTGATGCTTTGAATAGCATCACCAAAACTGGACTTGGCCTTGTGAACCCTGAACCCTGGAACGCTTGGA
1121 ATGAACAACACTCGTATCTGCGTCTGCTGGTGTTGATGGAGTTAAAGTTGATGTTCAAAACATTCTTGAGACGCTTGGA
1201 GCAGGTCATGGTGAAGAGTTAAACTTGCTAGAAAATACCAGGCTCTTGAGGCATCGATTCCCGAAACTTTCAAGA
1281 TAACGGAATCATTTCGTGTATGAGTCATAATGCCGATGGTTTATACAGTTCAAAGAGAAATGCTGTTATTCGAGCATCGG
1361 ATGATTTTTGGCCTAGAGATCCAGCAGTCATCACGACGATTGCTTACAACTCCTTATTCTTGGGAG
1441 TTTATGCAGCCAGATTGGGATATGTTTCATCATGACAAGCCTGGTCAACATGACTTCAACTCGACGAGCAGCTCGTCGTGCCGTGGGAGG
1521 ATGTGCTATATATGTCAGTGACAAGCCTGGTCAACATGACTTCAACTCTTTGAAGAAGCTTGTCCTCCCTGATGGTCTA
1601 TTCTGAGAGCTAAGCTCCCCGACGACGGCCGACAAGGACTGCCTTTTAACTGCCAAGGAGCAGGATGGTTAAGGTTGGAAA
1681 AAGATTGGAATTTGAATGATCTATCTGAGTTGTTGGGTTCTTTGGGGTTTATTCGAGCAAAAGATGTTAGTTATCTATGGAAGA
1761 GAAAAACCTCATTCACGACGAGAATCCAGACGCGATCTCTCCCATCTTGCTGGAGAAGTTGTTTACCTGCCACAAGATGCA
1841 TTGCAGGCGAGTCCAATAACCTTGAAGCCTGACAGCAGTGAGTTCAACTGGGATCTTGTTCCTGTCAAGGAACTAGTTAATGACATCAA
1921 TCGATGCCAATAACCTTGAAGCCTGACAGCAGTGAGTTCAACTGGGATCTTGTTCCTGTCAAGGAACTAGTTAATGACATCAA
2001 GTTTGCTCCTATAGGTTTGATCAAGATGTTCAACTCTTGGGGAGCAGTGAAAGAAATGAACCATCAACCTGAAGTTCGA
2081 ATGTGTCGCTGAAAGTTCGGGGTTCTGGGCCATTCGGGCCATATTCCTCGAGCAAACCGAAGCGTGTAGCAGTCGACTCG
2161 GAGGAGGTAGAGTTCATGTATGATGAGGGTGGTTTAATCACCATTGACTTGACTTGAAGTTGAAGTACCAGAGAAAAGAGTTGTACCTTTG
2241 GGATATAAGAATTGAACTA
```

Figure 1b

```
  1 MTVGAGITISDANLTVLGNRVLSDVHNNITLTAAPGGGVMNGAFIGVQSDQIGSRRVFPIGKLIGLRFLCAFRFKLWWMT
 81 QRMGCSGQEVPFETQFLVVETRDGSNIAGNGEEGDAVYTVFLPILEGDFRAVLQGNDNNEIEICLESGDPSVDGFEGSHL
161 VFVGAGSDPFETITYAVKSVEKHLQTFAHRERKKMPDILNWFGWCTWDAFYTDVTSDGVKKGLESFENGGIPPKFVIDD
241 GWQSVAKDATSADCKADNTANFANRLTHIKENYKFQKDGKEGERIENPALGLQHIVSYMKEKHATKYVVWHAITGYWGG
321 VSAGVKEMEQYESKIAYPVASPGVESNEPCDALNSITKTGLGLVNPEKVENFYNEQHSYLASAGVDGVKVDVQNILETLG
401 AGHGGRVKLARKYHQALEASISRNFQDNGIISCMSHNTDGLYSSKRNAVIRASDDFWPRDPASHTIHIASVAYNSLFLGE
481 FMQPDWDMFHSLHPMAEYHGAARAVGGCAIYVSDKPGQHDFNLLKKLVLPDGSILRAKLPGRPTKDCLFTDPARDGKSLL
561 KIWNLNDLSGVVGVFNCQGAGWCKVGKKNLIHDENPDTITGVIRAKDVSYLWKIAGESWTGDAVIFSHLAGEVVYLPQDA
641 SMPITLKPREFDVFTVVPVKELVNDIKFAPIGLIKMFNSGGAVKEMNHQPGSSNVSLKVRGSGPFGAYSSSKPKRVAVDS
721 EEVEFMYDEGGLITIDLKVPEKELYLWDIRIEL
```

Figure 1c

```
   1 ATGACGCGTCACACCGAAAATTTCTGTCAACGATGGCAACTTGGTGTGGTTCACGGGAAGACCATACTGACTGGGGTTCCTGA
  81 CAACATTGCTGCTGACCCCAGGATCTGGTGTTTTAGAGGGCCTTGGACTCGTTGCTGGCGCTTTCATTGTGCCACTGCTTCGAACAGTAAAA
 161 GTCTACATGTTTTCCCAGTCGGTGTTTAGAGGACACATCCGAGGTTCCCTATGTTGTTTCCGTTCAAGTTATGGTGGATGACC
 241 CAAAGAATGGGAACATCTCTGAGACACACGTTCCTCCTTCCTTCCTGCTGATGGAGAGCAAGTTCCGTGCTGCCCTGCAAGGAGA
 321 GGATCCTGATAATTCTCGACCATCTACACCGTTCTCCTTCCTTCCTTGAGGGCCAGTTCGAGAGCCAGTTCCGTGCTGCCCTGCAAGGAA
 401 ATGAAAAGAATGAGAGATTGCCTCGAGAGTGGAGATAACACTGTTGAGACCAACCAAGGACTTTCTCTTGTCTAT
 481 ATGCATGCTGGGACAAATCCCTTTGAAGTTATCACTCAAGCAGTGAAGGCTGTTGAAAAGCATACGCAAACTTTCTACA
 561 TAGAGAGAAGAAAAGTTACCTTCCTTCCTGACTGGTTGGTTGGTGTACTTGGATGCTTTTACACTGATGTCACTG
 641 CTGAGGGTGTTGTGAAGGTCTCAAAAGCCTTTCAGAGGGAGGGGCACCTCCAAAGTTCTTAATCATAGATGATGGTTGG
 721 CAACAGATAGAAGCCAAACAAAAAGATGCTGATTGTGTTGTACAAGAGGGAGCACAGTTTGCAAGTAGGCTGTCTGAAT
 801 AAAAGAAAATCATAAGTTTCAGAAAAATGGAATAACTATGCAGTTCCCAGGCCTAAAGGTGGTGTGAACCAGACAAGTCCA
 881 AGAAACAACACAAGTAAAATTGTGTATGCATGGCATGCTTTGGCTGCACCGGTCCAGTCGCTTTCAGTCACCGGTATGTTGGGCAACCAAGACATAGTTGT
 961 GGCATGGAGCATTATGATTCGCGCTTTGGCCTTGGCATTGCATTGGCCCTTGTGCATCATCCAAAGAGAAAGTTTCATTCTATAAGAGCTTCATTCCTACT
1041 AGACAGCTTCCTGTGGTATCGTGATGGCGTAAAGTTGATGCGCAAAACATTATTGAAACCCTCGGTGCTGCTCATGGTGGCAGG
1121 TGGCTTCCTGTGTTACACTTACTCGTAGCTACCATGACTCTACATTCTTGAAGCTTCGATTGCTCTCCTAACTTTTCTGACAATGGATGCATTGCTTG
1201 GTTACACTTACTCGTAGCTACCACACTGACAGTGCCAAACAGACTGCGGGTCGTGAGAGCTTCTGATGACTATTACCCTCGTG
1281 TATGTGCCACACAGTCTCCACAACCTGACCAGTTCATATTCTTCTGTGCTTACAGTTCTCTTTCCTTGGAGAGTTCATGCAGCCTGACTGG
1361 ATCCTGCCTCCACACGTAGTTTACATCCGACAGCAGAGTATCACGGTGCTGCTGCTGTCCTTCGTGATCAGTTCTTCGTGCTCAGTTAC
1441 GATATGTTCCATAGTTTACATCCGACAGCAGAGTATCACGGTGCTGCTGCTGTCCTTCGTGATCAGTTCTTCGTGCTCAGTTAC
1521 TGACAAACCAGTAACCACAGTTTGACCTGTTGTTCAACGATCCAGCTAGAGATCCAGCTAGAGATGCCAGCTAGAGAAAATGAAC
1601 CTGGCCCGACCGACGTGACTTCTTTGTTCAACGATCCAGCTAGAGATCCAGCTAGAGAAAAGAAAACTCGCATTCACGA
1681 AAATGTTCTGGTGTTGTTGGAGTATTCAATTGCCAAGGTGCCAGGATCAGAAGTGCCAGGATGCTATTTCGCAGTTGATGTTCAGTTGCCAGTGGA
1761 CGAGTCTCCGGGTACACTCACTGAGTGCTAACATGTTCTCTCCCAACGTCCTCGAAATGATCGACCTCGAAATGATCGACCTTGTGTCGATGTGGACAAGGTCGATGTGGACACGA
1841 AGGGTGATACTATTGTTTATGCCTATCGATCAGGGATTTGATTCGAATTCGAACATCTCATTGCACCAATTGGTCT
1921 AAAGTTTGGAATATGATCTTTCTCCATATTTCCTGAACAAGTTAATGTCCAAGTGGTCGAACCAATACCAGAGTTCGATGGTG
2001 ACTTGACATGTTCAACACGTGGTGCTGTCAGCGGTAACATGTTCTCTCCCAACGTCCTCGAAATGATCGACCTTGTGTCGATGTGGACAAGGTCGATGTGGACACGA
2081 AAGTTGCTTCTGAGCTAACATGTTCTCTCCCAACGTCCTCGAAATGATCGACCTTGTGTCGATGTGGACAAGGTCGATGTGGACACGA
2161 AGAAGGTTTGGTCTCTATACTCGTCACCTTGAGCTAGTGTAATGGCAAAGAAAATGTATAGATGAGGAAAATGTATAGATGAACATTGAAATTCAAGTT
2241 GGTCACAGGGTAGTCACCTTCGAAATTCCTATCCCGACGGAGGAAATGTATAGATGAACATTGAAATTCAAGTT
```

Figure 1d

```
  1 MTVTPKISVNDGNLVVHGKTILTGVPDNIVLTPGSGLGLVAGAFIGATASNSKSLHVEPVGVLEGTRFLCCFREKLWWMT
 81 QRMGTSGRDIPFETQFLLMESKGNDGEDPDNSSTIYTVFLPLLEGQFRAALQGNEKNEMEICLESGDNTVETNQGLSLVY
161 MHAGTNPFEEVITQAVKAVEKHTQTFLHREKKKLPSFLDWFGWCTWDAFYTDVTAEGVVEGLKSLSEGGAPPKFLIIDDGW
241 QQIEAKPKDADCVVQEGAQFASRLSGIKENHKFQKNGNNYDQVPGLKVVVDDAKKQHKVKFVYAWHALAGYWGGVKPASP
321 GMEHYDSALAYPVQSPGMLGNQPDIVVDSLAVHGIGLVHPKKVENEYNELHSYLASCGIDGVKVDVQNIIETLGAGHGGR
401 VTLTRSYHQALEASIARNFSDNGCIACMCHNTDSLYSAKQTAVVRASDDYYFRDPASHTIHISSVAYNSLFLGEFMQPDW
481 DMFHSLHPTAEYHGAARAIGGCAIYVSDKPGNHNFDLLKKLVLPDGSVLRAQLPGRPTRDSLFNDPARDGTSLLKIWNMN
561 KCSGVVGVENCQGAGWCRITKKTRIHDESPGTLTTSVRAADVDAISQVAGADWKGDTIVYAYRSGDLIRLPKGASVPVTL
641 KVLEYDLLHISPLKDIASNISFAPIGLLDMENTGGAVEQVNVQVVEPIPEFDGEVASELTCSLPNDRPPTATITMKARGC
721 RRFGLYSSQRPLKCSVDKVDVDFVYDEVTGLVTFEIPIPTEEMYRWNIEIQV
```

Figure 2 page 1/2

```
Cuc mel Aga1    ----------------------MTVGAGITISDANLTVLG-NRVLSDVHNNITLTAAPGG-----------------GVMNGAFIGVQSD-QI
At NP_175970    ----------------------MTVGAGISVTDSDLVVLG-HRVLEGVPENVLVTPASGN-----------------ALIDGAFIGVTSD-QT
At CAB66109     ----------------------MTITSNISVQNDNLVVQG-KTILTKIPDNIILTPVTGN------------------GFVSGSFIGATFE-QS
Bo X79330       ----------------------MTITSNISVQNDNLVVQG-KTILTKIPDNIILTPVAGA------------------GSDSGAFIGATFK-QS
Cuc mel Aga2    ----------------------MTVTPKISVNDGNLVVHG-KTILTGVPDNIVLTPGSGL------------------GLVAGAFIGATAS-NS
Pa CAB77245     ----------------------MTVTPKISINDGNLVVHG-KTILTGVPDNIVLTPRTGD------------------GLVAGCFIGATAS-ES
Hv S27762       ----------------------MTVTPQITVGDGRLAVRG-RTVLSGVPDNVTAAHAAGA-----------------GLVDGAFVGATAA-EA
                                       **    *      ***     *    *                              * *    *

Ps CAC38094     -MAPPLN--STTSNLIKTE------------SIFDLSERKFKVKG-FPLFHDVPENVSFRSFSSICKPSESNAPPSLLQKVLAYSHKGGFFGFSHE-TP
Va CAB64363     -MAPPNDPVNATLGLEPSE---------KVFDLSDGKLTVKG-VVLLSHVPENVTFSSFSSICVPR--DAPSSILQRVTAASHKGGFLGFSHV-SP
At AAD22659     -MAPLHESLSSINDVIESKPLFVPITKPILQPNSFNLSEGSLCAKDSTPILFDVPQNVTFTPFSSHSIST--DAPLPILLRVQANAHKGGFLGFTKE-SP
At BAB11595     -ASPCLTKSDS------GING-------VDFTEKFRLEDSTLLANG-QVVLTDVPVNVTLTSSPYL-VDK-------D--GVPLDVSAGSFIGFNLDGEP
Cs E15707       -MAPSFKNGGSNVVSFDGLN--------DMSSPPFAIDGSDFTVNG-HSFLSDVPENIVASPSPYTSIDK-------S------PVSVGCFVGFDAS-EP
                 :           :     .       .: :.*    .                    * .    **

Cuc mel Aga1    GSRRVFPIGKLIGLRFLCAFRFKLWWHTQRMGCSGQEVPPFETQFLVVETRDGSNIAGNGEE---GDAVYTVFLPILEGDFRAVLQGNDNNEIEICLESGD
At NP_175970    GSHRVFSLGKLEDLRFMCVFRFKLWWHTQRMGTNGKEIPCETQFLIVEANQGSDLGGRDQ-----SSSYVVFLPILEGDFRAVLQGNEANSLEICLESGD
At CAB66109     KSLHVFPIGVLEGLRFMCCFRFKLWWMHTQRMGSCGKDIPLETQFMLLESKDEVEGNGDD-----APTVYTVFLPLLEGQFRAVLQGNEKNEIEICLESGD
Bo X79330       KSLHVFPIGVLEGLRFHCCFRFKLWWMHTQRMGASGKDIPLETQFMLLESKDEVN--GDD-----APTVYTVFLPLLEGQFRAVLQGNEKNEIEICLESGD
Cuc mel Aga2    KSLHVFPVGVLEGTRFLCCFRFKLWWMHTQRMGTSGRDIPFETQFLLMESKGNDGEDPDN-----SSTIYTVFLPLLEGQFRAALQGNEKNEMEICLESGD
Pa CAB77245     ESIHVFPMGTLEGLRFTCCFRFKLWWMHTQRNGMCGKDVPLETQFMLIESKDGAAAIDDPESE--APTIYTVFLPLLEGQFRAVLQGNESNQIEICLESGD
Hv S27762       KSHHVFTFGTLRDCRFMCLFRFKLWWMTQRMGTSGRDVPLETQPILIEVPAAAGNDDGDSSDGDSEPVYLVMLPLLEGQFRTVLQGNDQDELQICIESGD
                .*  ** **   *  **  ***** ****** ***      *  *:           ***  ** **   **  :**

Ps CAC38094     SDRLMNSIGSFNGKDFLSIFRFKTWWSTQWIGKSGSDLQMETQWILIEVPETKS---------------YVVIIPIIEKCFRSALFPGFNDHVKIIAESGS
Va CAB64363     SDRLINSLGSFRGRNFLSIFRFKTWWSTQWVGNSGSDLQMETQWILIEVPETES---------------YVVIIPIIEKSFRSALEPGSDDEVKICAESGS
At AAD22659     SDRLTNSLGRFEDREFLSLFRFKMWWSTANIGKSGSDLQAETQWVMLKIPEIDS---------------YVAIIPTIEGAFRASLTPGEKGNVLICAESGS
At BAB11595     KSHHVASIGKLKNIRFMSIFRFKVWWTTHWVGSNGRDIENETQIIILDQSGSDSGPGSG-----SGRPYVLLLPLLEGSFRSSFQSGEDDDVAUCVESGS
Cs E15707       DSREVVSIGKLKDIRFMSIFRFKVWWTTHWVGRNGGDLESETQIVILEKS--DSG-------------RPYVFLLPIVEGPFRTSIQPGDDDFVDVCVESGS
                      : .  ..* : .  *. **** ** **                                     ::* :*  **:  :   . .: .  ***.

Cuc mel Aga1    PSVDGFEGSHLVFVGAGSDPFETITYAVKSVEKHLQTFAHRERKKMPDILNWFGWCTWDAFYTDVTSDGVKKGLES------------FENGGIPPKFV
At NP_175970    PTVDQFEGSHLVFVAAGSDPFDVITKAVKAVEQHLQTFSHRERKKMPDHLNWFGWCTWDAFYTNVTAKDVKQGLES------------LKAGGVTPKFV
At CAB66109     KAVETSQGTHLVYVHAGTNPFEVIRQSVVAVERHMQTFHHRSKKKLPSFVDWFGWCTWDAFYTDVTAEGVDEGLKS------------LSEGGTPPKFL
Bo X79330       KAVGTSQGTHLVYVHAGTNPFEVITQSVKAAERQMQTFHHRSKKKLPSFVDWFGWCTWDAFYTDVTAEGVDEGLKS------------LSEGGTPPKFL
Cuc mel Aga2    NTVETNQGLSLVYMHAGTNPFEVITQAVKAVEKHTQTFLHREKKKLPSFLDWFGWCTWDAFYTDATAEGVVEGLKS------------LSEGGAPPKFL
Pa CAB77245     CAVRTNQGMYLVYMHAGTNPFQVINQAVKAVEKHLYSFQHLEKKKIPSFLDWFGWCTWDAFFTDVTDEGVEEGLKS------------LSGGGTVPPRFL
Hv S27762       KAVETEQGMNNVVYHAGTNPFEDTITQAVKAVEKHTQTFHHREKKTVPSFVDWFGWCTWDAFYTDVTADGVKQGLRS------------LAEGGAPPRFL
                    .   *  ** * **:* **  : *     ****  ** :**       ****       **    *  ::

Ps CAC38094     TKVKESTFNSIAYVHFSENPYDLMKEAYSAIRVHLNSFRLLEEKTIPNLVDKFGWCTWDAFYLTVNPIGIFEGLDD------------FSKGGVEPRFV
Va CAB64363     TQVRASSFGAIAYVHVAETPYNLMREAYSALRVELDSFRLLEEKTVPRIVDKFGWCTWDAFYLTVNPVGVWHGLKD------------FSEGGVAPRFV
At AAD22659     TKVKESSFKSIAYIHICDNPYNLMKEAFSALRVEHNNTFKLLEESKKLFKIVDKFGWCTWDACYLTVDPATIWTGVKE----------FEDGGVCPKFV
At BAB11595     TEVTGSEFRQIVYVHAGDDPFKLVKDAMKVIRVEHNNTFKLLEEKSPPGIVDWFGWCTWDAFYLTVNPDGVHKGVKC----------LVDGGCPPGLV
Cs E15707       SKVVDASFRSMLYLHAGDDPFALVKEAMKIVRTHLGTFRLLEEKTPPGIVDKFGWCTWDAFYLTVKPQGVIEGVRH----------LVDGGCPPGLV
                   .      ::    *:   :      :      .   *  ***** * :*  * *:

Cuc mel Aga1    IIDDGWQSVAKDAT-----SADCKADNTANFANRLTHIKENYKFQKDGKE----------------GERIENPA-----------
At NP_175970    IIDDGWQSVGMDET-----SVEFNADNAANFANRLTHIKENEKFQKDGKE----------------GHRVDDPS-----------
At CAB66109     IIDDGWQQIENKEK-----DENCVVQEGAQFATRLVGIKENAKFQKSDQ------------------KDTQV-------------
Bo X79330       IIDDGWQQIENKEK-----DSNCLVQEGAQFATRLVGIKENAKFQKNDP------------------KDTQV-------------
Cuc mel Aga2    IIDDGWQQIEAKPK-----DADCVVQEGAQFSRLSGIKENHKFQKNGN-------------------NYDQV-------------
Pa CAB77245     IIDDGWQQIGSEETK--DDSNCVVXEGAQFASRLTGIKENDKFQKNG-------------------KSEEV-------------
Hv S27762       IIDDGWQQIGSENK---DDPGVAVQEGAQFASRLTGIRENTKFQSEH--------------------NQEET-------------
                *******             ** **  ** **  *** ***

Ps CAC38094     IIDDGWQSISFDGYDPNEDAKNLVLGGEQMSGRLHRFDECYKFRKYESGLLLGPNSPPYDPNNFTDLIKGIEHEKLRKKREEAISSKSSDLAEIESKIK
Va CAB64363     VIDDGWQSVNFDDDEDPNEDAKNLVLGGEQMTARLHRFEEGDKFRYQKGLLLGPNAPSFNPETIKELTSKGIEAEHLG-KQAAAISAGGSDLAEIEIMIV
At AAD22659     IIDDGWQSINFDGDELDKDAENLVLGGEQMTARLTSFKECKKFRNYKE---------------ESLG---------S--------
At BAB11595     LIDDGWQSIGHDSDGIDVEGMNITVAGEQMPCRLLKFEENHKFKDYVS---------------P-----------KDQ--------
Cs E15707       LIDDGWQSIGHDSDPITKEGHNQTVAGEQMPCRLLKFQENYKFRDYVN----------P-----------KATG-------
                :*****.:         **    ** .**        *:* **:.

Cuc mel Aga1    ----------------------LGLQHIVSYMKEKHA-TKYVYVWHAITGYWGGVSAGVKEMEQYESKIAYFVASPGVESNEPCDALNSITK
At NP_175970    ----------------------LSLGHVITDIKSNNS-LKYVYVWHAITGYWGGVRPGVSGMEHYESKVAYFVSSPGVMSSENCGCLESITK
At CAB66109     ----------------------SGLKSVVDNAKQRHN-VKQVYAWEALAGYWGGVKPAASGMEHYDSALAYFVQSPGVLGNQPDIVMDSLAV
Bo X79330       ----------------------SGLKSVVDNAKQRHN-VKQVYAWEALAGYWGGVKPRASGMEHYDSALAYFVQSPGVLGNQPDIVMDSLAV
Cuc mel Aga2    ----------------------PGLKVVVDDAKQHK-VKFVYAWEALAGYWGGVKPASPGMEHYDSALAYFVQSPGMLGNQPDIVVDSLAV
Pa CAB77245     ----------------------PGLKLVVDDAKQHEN-VKFVYVWHALAGYWGGVKPPAAGMEHYDTALAYFVQSPGVMGNQPDIVMDSLSV
Hv S27762       ----------------------PGLKRLVDETKKEHG-VKSVYVWHAMAGYWGGVKPSAAGMEHYEPALAYFVQSPGVTGNQPDIVMDSLSV
                                          * **  ***   *** **

Ps CAC38094     KVVKEIDDLFGGEQFSSGEKS----EMKSEYGLKAFTKDLRTKFKGLDDVYWHALCGAWGGVRPETTH---LDTKIVPCKLSPGLDGTMEDLAVVEISK
Va CAB64363     KVREEIDDLFGGKGKESNESGGCCCKAAECGGMKDFTTDLRTEFKGLDDVYWHALCGGWGGVRPGTTH---LDSKIIPCKLSPGLVGTMKDLAVDKIVE
At AAD22659     ------DDVSG------S---G-----------MAAFTKDLRLRFKSLDDIYWHALCGAWNGVRPETMMD---LKAKVAPFELSPSLGATMADLAVDKVVE
At BAB11595     --------------NDVG--------MKAFVRDLKDEFSTVDYIYWHALCGYWGGLRPEAPAL--PPSTIIRPELSPGLKLTMEDLAVDKIIE
Cs E15707       -----------PR---AGQKG----------MKAFIDELKGEFKTVEHVYWHALCGYWGGLRPQVPGL--PEARVIQPFVLSPGLQMTMEDLAVDKIVL
                     :    :       *  .  .  *.***: * *.*: .      . :  **.:      :  .:
```

Figure 2 page 2/2

```
Cuc mel Aga1    TGLGLVNPEKVFNFYNEQHSYLASAGVDGVKVDVQNILETLGAGHGGRVKLARKYHQALEASISRNFQDNGIISCMSHNTDGLYS-SKRNAVIRASDDFW
At NP_175970    NGLGLVNPEKVFSFYNDLHSYLASVGVDGVKVDVQNILETLGAGHGGRVKLARKYHQALEASISRNFPDNGIISCMSHNTDGLYS-AKKTAVIRASDDFW
At CAB66109     HGLGLVNPEKVFNFYNELHSYLASCGIDGVKVDVQNIIETLGAGLGGRVSLTRSYQQALEASIARNFTDNGCISCMCHNTDGLYS-AKQTAIVRASDDFT
Bo X79330       HGLGLVNPEKVFNFYNELHSYLASCGIDGVKVDVQNIIETLGAGLGGRVSLTRSYHQALEASIARNFKDNGCISCMCHNTDGLYS-AKQTAIVRASDDYY
Cuc mel Aga2    HGIGLVHPEKVFNFYNELHSYLASCGIDGVKVDVQNIIETLGAGHGGRVTLTRSYHQALEASIARNFSDNGCIACMCHNTDSLYS-AKQTAVVRASDDYY
Pa CAB77245     HGLGLVHPRKVFNXYNELHAXLXSCGVNGVKVDVQNIIETLGAGHGGRVSLTRSYIQALEGSIARNFPDNGCIACMCHNTDSIYS-AKQTAVVRASDDFT
Hv S27762       LGLGLVHPRRVERFYDELHAYLAACGVDGVKVDVQNIVETLGAGHGGRVALTRAYHRALEASVARNFPDNGCISCMCHNTDMLYS-AKQTAVVRASDDFY Ps CAC38094     ASLGLVHPSQANELYDSMHSYLAESGITGVKVDVIHSLEYVCDEYGGRVDLAKVYYEGLTKSIVKNENGNGMIASHQHCNDFFFLGTKQISMGRVGDDFW
Va CAB64363     GSIGLVHPEQANDLTDSMHSYLAQTGVTGVKVDVIHSLEYVCSEYGGRVEIAKAYYDGLTNSIIKNFNGSGIIASMQQCNDFFFLGTKQIPFGRVGDDFW
At AAD22659     AGIGLVHPSKAHEFYDSMHSYLASVGVTGAKIDVFQTLESLAEEHGGRVELAKAYYDGLTESMIKNFNGTDVLASMQQCNEFFFLATKQISIGRVGDDFW
At BAB11595     TGIGFASPDLAKEFYEGLHSHLQNAGIDGVKVDVIHILEMLCQKYGGRVDLAKAYFKALTSSVNKHFNGNGVIASHEHCNDFMFLGTEAISLGRVGDDFW
Cs E15707       HKVGLVPPEKAEEMYEGLHABLEKVGIDGVKIDVIHLLEMLCEDYGGRVDLAKAYYKAMTKSINKHFKGNGVIASMEHCNDFMFLGTEAISLGRVGDDFW
                  *:.  *   .    *:   *: *.*;**  :*  .     ****  :::  *  .:  *::: *  ...  *:.*  :  .:  ::    *..**::

Cuc mel Aga1    PRDPAS--------HTIHIASVAYNSLFLGEFMQPDWDMFHSLHPMAEYHGAARAVGGCAIYVSDKPG--QHDFNLLKKLVLPDGSILRAKLPGRPTKDC
At NP_175970    PRDPAS--------HTIHIASVAYNTLFLGEFMQPDWDMFHSLHPMAEYHAAARAVGGCAIYVSDKPG--QHDFNLLRKLVLRDGSILRAKLPGRPTSDC
At CAB66109     PRDPAS--------HTIHIASVAYNSLFLGEFMQPDWDMFHSLHPTAEYHAAARAVGGCAIYVSDKPG--NHNFDLLRKLVLPDGSVLRAKLPGRPTRDC
Bo X79330       PRDPAS--------HTIHIASVAYNTLFLGEFMQPDWDMFHSLHPTAEYHAAARAVGGCAIYVSDKPG--NHNFDLLKKLVLPDGSVLRARLPGRPTRDS
Cuc mel Aga2    PRDPTS--------HTIHISSVAYNSLFLGEFMQPDWDMFHSLHPTAEYHGAARAVGGCAIYVSDKPG--NHNFDLLKKLVLPDGSVLRAQLPGRPTRDS
Pa CAB77245     PRDPAS--------HTIHVSSVANNSLFLGEFMQPDWDMFHSLHPAAEYHGAARAVGGCPIYVSDKPG--HHNFELLKKLVLPDGSVLRARLPGRPTRDS
Hv S27762       PRDPAS--------HTVHISSVAYNTLFLGEFMQPDWDMFHSLHPAASYHGAARAIGGCPIYVSDKPG--NHNFDLLRKLVLPDGSVLRAQLPGRPTRDC
                ****  *        ** *  *** *  ***************** **** **** *  *********  *  * ******** *** *** *** **

Ps CAC38094     FQDPNGDFMGSFWLQGVHMIHCSYNSLWMGQMIQPDWDMFQSDHVCAKFHAGSRAICGGPIYVSDNVG--SHDFDLIKKLVFPDGTIPKCIYFPLPTRDC
Va CAB64363     FQDPNGDFMGVFWLQGVHMIHCSYNSLWMGQIIQPDWDMFQSDHECAYFHAGSRAICGGPVYVSDSVG--SHDFDLIKKLVFPDGTVPKCIYFPLPTRDC
At AAD22659     WQDPYGDPQGVYWLQGVHMIHCSYNSIWMGQMIQPDWDMFQSDHVCAETHAASRAICGGPVVTLSDHLGKASHNFDLIKKLAFFDGTIPRCVHYALPTRDS
At BAB11595     CTDPSGDFNGTFWLQGCHMVHCANVSLWMGNFIQPDWDMFQSTHPCAEFHAASRAISGGPIYISDCVG--KHDFDLLKRLVLPNGSILRCEYYALPTRDR
Cs E15707       CTDPSGDFNGTFWLQGCHMVHCANDSLWMGNFIHPDWDMFQSTHPCAAFHAASRAISGGPIYVSDSVG--KHNFDLLKKLVLPDGSILRSEYYALPTRDC
                  **  *      :  *:::****;  *  *   ****  ** * *    **  * *** *         *  * *  *     *   *

Cuc mel Aga1    LFTDPARDGKSLLKIWNLNDLSGVVGVFNCQGAGWCKVGKKNLIHDENPDTITGVIRAKDVSYLWKIAG----ESWTGDAVIFSHLAGEVVYLPQ-DASH
At NP_175970    FFSDPVRDNKSLLKIWNLNEFTGVIGVFNCQGAGWCKNEKRYLIHDQEPGTISGCVRTNDVHYLHKVAA----FEWTGDSIVYSHLRGELVYLPK-DTSL
At CAB66109     LFADPARDGTSLLKIWNMNKFTGIVGVFNCQGAGWCKSTKKNQIHDTSPGTLTGSIRADDADLISQVAG----EDWSGDSIVYAYRSGEVVRLPK-GASI
Bo X79330       LFADPARDGTSLLKIWNMNKFTGIVGVFNCQGAGWCKDTKKNRIHDTSPGTLTGLVRAEDADLISEVAG----QDWGGDSIVYAYKSGELVRLPK-GASI
Cuc mel Aga2    LFNDPARDGISLLKIWNMNKCSGVVGVFNCQGAGWCKITTKKTRIHDEAAPGTLSGSIRAHDVEFINQLAG----QDWNGEVIVFTYGGSGEVVRLPK-CASI
Pa CAB77245     LFVDPARDGVSLLKIWNMNKCLGVVGVFNCQGAGWCKITKKTRIHDAAPGTLSGSIRAHDVSFINQLAG----QDWNGEVIVFTYGGSGEVVRLPK-CASI
Hv S27762       LFSDPARDGASLLKIWNMNKCAGVVGVFNCQGAGWCRVAKKTRIHDEAPGTLTGSVRAEDVEAIAQAAGT---GDWNGEAVVYAHRAGELVRLPR-GATL
                *  **  *    ************    *  ************     *     **     *          *    **                 *

Ps CAC38094     LFKNPLFDHTTVLRIWMFNKYGGVIGAFNCQGAGWDPIKQKFRGFPECYKPIPGTVHVTEVEWDQ--KEETSHLGKAEEYVVYLNQAEELSLHTLKSEPI
Va CAB64363     LFRNPLFDQKTVLKIWMFNKYGGVIGAFNCQGAGWDPKGKKFKGFPECYKAISCTVHVTEVEWDQ--KKEAEHMGKAEEYVVYLNQAEVLHLHTPVSEPL
At AAD22659     LFKNPLFDKESILKIFNFNKFGGVIGTFNCQGAGWSPEEHRFKGYKECYTTVSGTVHVSDIEWDQNPEAAGSQVTYTGDYLVYKQQSEEILFMNSKSEAM
At BAB11595     LFEDPLHDGKTHLKIWNLNKYTGVIGAFNCQGGGWCRETRRNQCFSECVNTLTATTSPKDVEWNS--GSSPISIANVEEFALFLSQSKKLLLSGL-NDDL
Cs E15707       LFEDPLHNGSTMLKIWNLNKFTGVIGAFNCQGGGWCRETRRNQCFSQYSKRVTSKTNPKDIEWHS--GENPISIEGVKTFALYLYQAKKLILSKP-SQDL
                *  *         ** *  *      * ***  **    **:

Cuc mel Aga1    PITLKPREFDVFTVVPVKELVND-IKFAPIGLIKMFNSGGAVKEMNHQP--------------------------NVSLKVRGSGPFGAYSSSK-P
At NP_175970    PVTLMPREYEVFTVVFVKEFSDG-SKFAPVGLMEMFNSGGAIVSLRYDDEGTKF--------------------VVRMKLRGSSGLVGVYSSVRRP
At CAB66109     PLTLKVLEYELFHISPLKEITEN-ISFAPIGLVDMFNSSGAIESIDINHVTD--KNPEFFDGEISSASPALSDNRSPTALVSVSVRGCGRFGAYSSSQR-P
Bo X79330       PLTLKVLEYELFHISPLKEITAS-ISFAPIGLLDMFNSSGAIQSMEINTVTD--EKP-----ELSSSS-VVSENRSPTALISLGVRGCGRFGAYSSQR-P
Cuc mel Aga2    PVTLKVLEYDLLHISPLKDIASN-ISFAPIGLLDMFNTGGAVEQNVN-QVVE--PIPEFDGEVASELTCSLPNDRPPTATITMKARGCRRFGLYSSQR-P
Pa CAB77245     PVTLEVLEYELXHICFVKEITSN-ISFAPIGLLDMFNSGGAVEQFDVRMDSNNAEPPLFDGKVASKLSSSLSNNQSPSATVVLRVRGCGRFGAYSSQR-P
Hv S27762       PVTLKRLEYELFHVCPVRAVAPG-VSFAPIGLLHMFNAGGAVEECTVETGED--------------G--------NAVVGLRVRGCGRFGAYCSRR-P
                *                *       ***   ***   **

Ps CAC38094     QFTIQPSTFELYSFVPVTKLCGG-IKFAPIGLTNMFNSGGTVIDLEYVGNG------------------------AKIKVKGGGSFLAYSSES-P
Va CAB64363     QLTIQPSTFELYNFVPVEKLGSSNIKFAPIGLTNMFNSGGTIQELEYIEKD------------------------VKVKVKGGGRFLAYSTQS-P
At AAD22659     KITLEPSAFDLLSFVPVTELVSSGVRFAPLGLINMFNCVGTVQDMKVTGDN--------------------------SIRVDVKGEGRFMAYSSSA-P
At_BAB11595_    ELTLEPFKFELITVSPVVTIEGNSVRFAPIGLVNMLNTSGAIRSLVYNDE-------------------------SVEVGVFGAGEFRVYASKK-P
Cs E15707       DIALDPFEFELITVSPVTKLIQTSLHFAPIGLVNMLNTSGAIQSVDYDDDLS----------------------SVEIGVKGCGEMRVFASKK-P
                .::  :::   *: .       ***;**  *;:*  *:: .

Cuc mel Aga1    KRVAVDSEEVEFNYD-EGGLITIDLKVPEKE--LYLWDIRIEL
At NP_175970    RSVTVDSDDVEYRYEPESGGLVTFTLGVPEKE--LYLWDVVIQ-
At CAB66109     LKCAVESTETDFTYDAEVGLVTLNLFVTREE--MFRWHVEILV
Bo X79330       LRCAVDGTETEFNYDAEVGLVTLNLFVTREE--MFRWRVEILV
Cuc mel Aga2    LKCSVDKVDVDFVYDEVTGLVTFEIPIPTEE--MYRWDIEIQV
Pa CAB77245     LKCTVDLVETEFNYDSVTGLVTLIIFVPDQE--MYKWSVEFQL
Hv S27762       AKCSVDSADVEFTYDSDTGLVTADVFVPEKE--MYRCALEIRV
                 *  *  .   * *  ** **      *     *

Ps CAC38094     KKFQLNGCEVDFEWLGD-GKLCVNVPWIEEA--CGVSDMEIFF
Va CAB64363     KKFQLNGSDAAFQWLPD-GKLTLNLAWIEEN--DCVSDLAIFF
At AAD22659     VKCYLNDKEAEFKWEEETGKLSFFVPWVSES--GGISHLSFTF
At_BAB11595     VSCLIDGEVVEFGY-ED-SMVMVQVPWSGPD---GLSSIQYLF
Cs E15707       RACRIDGEDVGFKYDQD-QHVVVQVPWPIDSSSGGISVIEYLF
                  :       . :  :                  :
```

|   | A |   | B |
|---|---|---|---|
| alk α-gal, RFO synthases | | | |
| Cyc mel α-gal-II | 198 DWFGWCTIDAFYTDATAEGVVEGLKSLSEGQ----APPKFLIIDDGHQ | 371 | CGIDGVREVDVQ |
| Hor vul | 203 DWFGWCTIDAFYTDVTADGVKQGLRSLAEGQ----APPRFLIIDDGHQ | 371 | CGVDGVREVDVQ |
| Cuc mel α-gal-I | 200 NWEGWCTIDAFYTDVTSDGVKKGLESFENGQ----IPPKFVIIDDGHQ | 377 | AGVDGVREVDVQ |
| Cuc sat RaS | 213 DKFGWCTIDAFYLTVHPQGVIEGVRHLVDGH----CPPGLVLIHDGHQ | 391 | VGIDGVREIDVI |
| Pis sat StS | 219 DKFGWCTIDAFYLTVPIGIFHGLDDESEGH----VEPRFVIIDDGHQ | 473 | SGITGVKVRVI |
| Family 27 | | | |
| Cof ara | 41 PPMGWNSWNHFERCNIDEKLIRETADAMVSKQLAALGYKYINLDDCWA | 137 | WGVDYLEYDNC |
| Cam tet | 56 PPMGWNSWNHFGCDINEMVVRETADAMVSTQLAALGYKYINLDDCWA | 162 | WGVDYLEYDNC |
| Ara tha | 70 PQMGWNSWNFFACNINETVIKETADALVSSQLADLGYILHVNIDDCWS | 182 | WGVDYLKYDNC |
| Asp nig_B | 27 PALGWNSWNAYSCDIDADKIVTAANEVVNLQLKDLGYEYINLDDCWS | 141 | WGIDYINLDGC |
| Sac cer | 30 PQMGWDNWNTEACDVSEQLLLDTADRISDLQLKDMGYKYIILDDCHS | 140 | NRVDYLEYDNC |
| Family 36 | | | |
| Esc col | 292 RPVHLNTWEGIYEHHNPDYIMQAERAAAIS----VEREFIIDDGWF | 443 | HPVDYVKDMN |
| Asp nig C | 348 RPVLLNSWEGVYFDYNQSSIETLAEESAAL----VRLFVMDDGWF | 500 | TGISYVKWDNN |
| Bac ste | 329 RPILINMWEATYFHFNEEKTLRLAKTAAELG----IELFVLIDDGWF | 470 | APISYVWDMN |
| Ped pxx | 323 IPSVLNTWETLTEAVSESKVQHLIEHAHQLS----LQMLVLDDGHF | 465 | NQLDYLWDMN |
| Bac_hal | 330 RPILLNSWEATYPDFTEDSLVEEAKEGKKLS----VELFVLDDGHF | 361 | APISYIKWDMN |
|   | W G DD W |   | sKD |

Figure 7

SEQUENCE LISTING

```
<160> NUMBER OF SEQ ID NOS: 49

<210> SEQ ID NO 1
<211> LENGTH: 13
<212> TYPE: PRT
<213> ORGANISM: Artificial sequence
<220> FEATURE:
<223> OTHER INFORMATION: Peptide derived from a purified C. melo
      alkaline-alpha-galactosidase

<400> SEQUENCE: 1

Glu Tyr Pro Ile Gln Ser Pro Gly Asn Val Ser Asn Leu
1               5                   10

<210> SEQ ID NO 2
<211> LENGTH: 9
<212> TYPE: PRT
<213> ORGANISM: Artificial sequence
<220> FEATURE:
<223> OTHER INFORMATION: Peptide derived from a purified C. melo
``` alkaline-alpha-galactosidase
<220> FEATURE:
<221> NAME/KEY: misc_feature
<222> LOCATION: (7)..(7)
<223> OTHER INFORMATION: Arginine or Leucine

<400> SEQUENCE: 2

Asp Ile Ser Leu Thr Glu Xaa Val Thr
1               5

<210> SEQ ID NO 3
<211> LENGTH: 17
<212> TYPE: PRT
<213> ORGANISM: Cucumis melo

<400> SEQUENCE: 3

Thr Val Gly Ala Gly Ile Thr Ile Ser Asp Ala Asn Leu Thr Val Leu
1               5                   10                  15

Gly

<210> SEQ ID NO 4
<211> LENGTH: 7
<212> TYPE: PRT
<213> ORGANISM: Artificial sequence
<220> FEATURE:
<223> OTHER INFORMATION: Conserved motif in seed imbibition protein
      (SIP) family

<400> SEQUENCE: 4

Trp Trp Met Thr Gln Arg Met
1               5

<210> SEQ ID NO 5
<211> LENGTH: 2259
<212> TYPE: DNA
<213> ORGANISM: Cucumis melo

<400> SEQUENCE: 5

| | | | | |
|---|---|---|---|---|
| atgacggttg | gtgctggaat | tactatctcc | gatgcgaatt | tgacggtgtt | gggaaatcgt | 60 |
| gttttatccg | atgttcataa | taacattact | ctcacggcgg | cgccgggtgg | tggtgtgatg | 120 |
| aacggcgcct | tcataggagt | tcaatctgat | cagatcggta | gtcgccgagt | ttttcctatt | 180 |
| gggaaattga | tagggttgag | attcttatgt | gcttttcgat | tcaaattatg | gtggatgact | 240 |
| caaagaatgg | ggtgttccgg | tcaagaagtt | ccattcgaga | cacaatttct | tgtggtggaa | 300 |
| acacgtgatg | gttctaacat | tgccggaaat | ggagaggaag | gcgatgccgt | ttatactgtt | 360 |
| tttcttccta | ttcttgaagg | cgatttcaga | gctgttcttc | aagggaatga | taataatgaa | 420 |
| attgaaatct | gtttagaaag | tggagatcca | agtgtagatg | ggtttgaggg | tagccatttg | 480 |
| gtgtttgtgg | gtgctggatc | agatcctttt | gaaaccatta | cttatgcagt | caagtctgtt | 540 |
| gaaaagcatt | tgcaaacttt | tgctcatcgc | gaaagaaaga | gatgcctga | tatttgaac | 600 |
| tggttcggct | ggtgcacatg | ggatgctttc | tacactgatg | tcacttcaga | tggcgtcaag | 660 |
| aagggtcttg | aaagctttga | gaatggagga | attcctccca | gtttgtcat | tatcgatgat | 720 |
| ggatggcaat | cagttgccaa | ggatgctact | agtgctgatt | gcaaagctga | taacacagca | 780 |
| aactttgcaa | acaggttaac | tcacataaaa | gagaattaca | aatttcaaaa | agatggcaaa | 840 |
| gagggtgaaa | gaattgagaa | ccctgcactg | ggtcttcaac | atattgtgtc | ctacatgaaa | 900 |
| gagaagcatg | cgaccaagta | tgtttatgtt | tggcatgcca | taacaggcta | ctggggtggt | 960 |
| gtgagtgctg | gagttaaaga | gatggaacaa | tatgagtcca | agattgcgta | cccggttgca | 1020 |

-continued

```
tctcctgggg tcgaatcaaa tgagccatgt gatgctttga atagcatcac caaaactgga    1080
cttggccttg tgaaccctga aaaggttttc aacttctaca atgaacaaca ctcgtatctt    1140
gcgtctgctg gtgttgatgg agttaaagtt gatgttcaaa acattcttga gacgcttgga    1200
gcaggtcatg gtggaagagt taaacttgct agaaaatacc atcaggctct tgaggcatcg    1260
atttcccgaa actttcaaga taacggaatc atttcgtgta tgagtcataa taccgatggt    1320
ttatacagtt caaagagaaa tgctgttatt cgagcatcgg atgattttg gcctagagat     1380
ccagcatctc acacgattca tatagcatca gttgcttaca actccttatt tcttggggag    1440
tttatgcagc cagattggga tatgtttcat agtcttcatc ctatggccga atatcacgga    1500
gcagctcgtg ccgtgggagg atgtgctata tatgtcagtg acaagcctgg tcaacatgac    1560
ttcaatcttt tgaagaagct tgtcctccct gatggttcta ttctgagagc taagctcccc    1620
ggacggccga caaggactg cctttttacg gatcctgcta gagatggaaa aagtctattg      1680
aagatttgga atttgaatga tctatctgga gttgttgggg tctttaactg ccaaggagca    1740
ggatggtgta aggttggaaa gaaaaacctc attcacgacg agaatccaga cacgatcacg    1800
gggttattc gagcaaaaga tgttagttat ctatggaaga ttgcaggcga gtcctggaca      1860
ggggatgcag tgatattctc ccatcttgct ggagaagttg tttacctgcc acaagatgca    1920
tcgatgccaa taaccttgaa gcctcgagag ttcgacgtct tcacggttgt tcctgtcaag    1980
gaactagtta atgacatcaa gtttgctcct ataggtttga tcaagatgtt caactctgga    2040
ggagcagtga agaaatgaa ccatcaacct ggaagttcga atgtgtcgct gaaagttcgg      2100
ggttctgggc cattcggggc atattcctcg agcaaaccga agcgtgtagc agtcgactcg    2160
gaggaggtag agttcatgta tgatgagggt ggtttaatca ccattgactt gaaggtacca    2220
gagaaagagt tgtacctttg ggatataaga attgaacta                            2259
```

<210> SEQ ID NO 6
<211> LENGTH: 753
<212> TYPE: PRT
<213> ORGANISM: Cucumis melo

<400> SEQUENCE: 6

```
Met Thr Val Gly Ala Gly Ile Thr Ile Ser Asp Ala Asn Leu Thr Val
1               5                   10                  15

Leu Gly Asn Arg Val Leu Ser Asp Val His Asn Asn Ile Thr Leu Thr
                20                  25                  30

Ala Ala Pro Gly Gly Gly Val Met Asn Gly Ala Phe Ile Gly Val Gln
            35                  40                  45

Ser Asp Gln Ile Gly Ser Arg Arg Val Phe Pro Ile Gly Lys Leu Ile
        50                  55                  60

Gly Leu Arg Phe Leu Cys Ala Phe Arg Phe Lys Leu Trp Trp Met Thr
65                  70                  75                  80

Gln Arg Met Gly Cys Ser Gly Gln Glu Val Pro Phe Glu Thr Gln Phe
                85                  90                  95

Leu Val Val Glu Thr Arg Asp Gly Ser Asn Ile Ala Gly Asn Gly Glu
                100                 105                 110

Glu Gly Asp Ala Val Tyr Thr Val Phe Leu Pro Ile Leu Glu Gly Asp
            115                 120                 125

Phe Arg Ala Val Leu Gln Gly Asn Asp Asn Glu Ile Glu Ile Cys
        130                 135                 140

Leu Glu Ser Gly Asp Pro Ser Val Asp Gly Phe Glu Gly Ser His Leu
```

-continued

```
            145                 150                 155                 160
        Val Phe Val Gly Ala Gly Ser Asp Pro Phe Glu Thr Ile Thr Tyr Ala
                        165                 170                 175
        Val Lys Ser Val Glu Lys His Leu Gln Thr Phe Ala His Arg Glu Arg
                        180                 185                 190
        Lys Lys Met Pro Asp Ile Leu Asn Trp Phe Gly Trp Cys Thr Trp Asp
                        195                 200                 205
        Ala Phe Tyr Thr Asp Val Thr Ser Asp Gly Val Lys Lys Gly Leu Glu
                        210                 215                 220
        Ser Phe Glu Asn Gly Gly Ile Pro Pro Lys Phe Val Ile Ile Asp Asp
        225                 230                 235                 240
        Gly Trp Gln Ser Val Ala Lys Asp Ala Thr Ser Ala Asp Cys Lys Ala
                        245                 250                 255
        Asp Asn Thr Ala Asn Phe Ala Asn Arg Leu Thr His Ile Lys Glu Asn
                        260                 265                 270
        Tyr Lys Phe Gln Lys Asp Gly Lys Glu Gly Glu Arg Ile Glu Asn Pro
                        275                 280                 285
        Ala Leu Gly Leu Gln His Ile Val Ser Tyr Met Lys Glu Lys His Ala
                        290                 295                 300
        Thr Lys Tyr Val Tyr Val Trp His Ala Ile Thr Gly Tyr Trp Gly Gly
        305                 310                 315                 320
        Val Ser Ala Gly Val Lys Glu Met Glu Gln Tyr Glu Ser Lys Ile Ala
                        325                 330                 335
        Tyr Pro Val Ala Ser Pro Gly Val Glu Ser Asn Glu Pro Cys Asp Ala
                        340                 345                 350
        Leu Asn Ser Ile Thr Lys Thr Gly Leu Gly Leu Val Asn Pro Glu Lys
                        355                 360                 365
        Val Phe Asn Phe Tyr Asn Glu Gln His Ser Tyr Leu Ala Ser Ala Gly
                        370                 375                 380
        Val Asp Gly Val Lys Val Asp Val Gln Asn Ile Leu Glu Thr Leu Gly
        385                 390                 395                 400
        Ala Gly His Gly Gly Arg Val Lys Leu Ala Arg Lys Tyr His Gln Ala
                        405                 410                 415
        Leu Glu Ala Ser Ile Ser Arg Asn Phe Gln Asp Asn Gly Ile Ile Ser
                        420                 425                 430
        Cys Met Ser His Asn Thr Asp Gly Leu Tyr Ser Ser Lys Arg Asn Ala
                        435                 440                 445
        Val Ile Arg Ala Ser Asp Asp Phe Trp Pro Arg Asp Pro Ala Ser His
                        450                 455                 460
        Thr Ile His Ile Ala Ser Val Ala Tyr Asn Ser Leu Phe Leu Gly Glu
        465                 470                 475                 480
        Phe Met Gln Pro Asp Trp Asp Met Phe His Ser Leu His Pro Met Ala
                        485                 490                 495
        Glu Tyr His Gly Ala Ala Arg Ala Val Gly Gly Cys Ala Ile Tyr Val
                        500                 505                 510
        Ser Asp Lys Pro Gly Gln His Asp Phe Asn Leu Leu Lys Lys Leu Val
                        515                 520                 525
        Leu Pro Asp Gly Ser Ile Leu Arg Ala Lys Leu Pro Gly Arg Pro Thr
                        530                 535                 540
        Lys Asp Cys Leu Phe Thr Asp Pro Ala Arg Asp Gly Lys Ser Leu Leu
        545                 550                 555                 560
        Lys Ile Trp Asn Leu Asn Asp Leu Ser Gly Val Val Gly Val Phe Asn
                        565                 570                 575
```

-continued

```
Cys Gln Gly Ala Gly Trp Cys Lys Val Gly Lys Lys Asn Leu Ile His
            580                 585                 590

Asp Glu Asn Pro Asp Thr Ile Thr Gly Val Ile Arg Ala Lys Asp Val
        595                 600                 605

Ser Tyr Leu Trp Lys Ile Ala Gly Glu Ser Trp Thr Gly Asp Ala Val
    610                 615                 620

Ile Phe Ser His Leu Ala Gly Glu Val Val Tyr Leu Pro Gln Asp Ala
625                 630                 635                 640

Ser Met Pro Ile Thr Leu Lys Pro Arg Glu Phe Asp Val Phe Thr Val
                645                 650                 655

Val Pro Val Lys Glu Leu Val Asn Asp Ile Lys Phe Ala Pro Ile Gly
            660                 665                 670

Leu Ile Lys Met Phe Asn Ser Gly Ala Val Lys Glu Met Asn His
        675                 680                 685

Gln Pro Gly Ser Ser Asn Val Ser Leu Lys Val Arg Gly Ser Gly Pro
    690                 695                 700

Phe Gly Ala Tyr Ser Ser Ser Lys Pro Lys Arg Val Ala Val Asp Ser
705                 710                 715                 720

Glu Glu Val Glu Phe Met Tyr Asp Gly Gly Leu Ile Thr Ile Asp
                725                 730                 735

Leu Lys Val Pro Glu Lys Glu Leu Tyr Leu Trp Asp Ile Arg Ile Glu
            740                 745                 750

Leu
```

<210> SEQ ID NO 7
<211> LENGTH: 6
<212> TYPE: PRT
<213> ORGANISM: Artificial sequence
<220> FEATURE:
<223> OTHER INFORMATION: Conserved motif in seed imbibition protein
      (SIP) family

<400> SEQUENCE: 7

```
Gly Tyr Trp Gly Gly Val
1               5
```

<210> SEQ ID NO 8
<211> LENGTH: 13
<212> TYPE: PRT
<213> ORGANISM: Artificial sequence
<220> FEATURE:
<223> OTHER INFORMATION: Conserved motif in seed imbibition protein
      (SIP) family
<220> FEATURE:
<221> NAME/KEY: misc_feature
<222> LOCATION: (7)..(7)
<223> OTHER INFORMATION: Iso-Leucine or Valine or Glycine

<400> SEQUENCE: 8

```
Val Asp Val Gln Asn Ile Xaa Glu Thr Leu Gly Ala Gly
1               5                   10
```

<210> SEQ ID NO 9
<211> LENGTH: 2316
<212> TYPE: DNA
<213> ORGANISM: Cucumis melo

<400> SEQUENCE: 9

```
atgacggtca caccgaaaat ttctgtcaac gatggcaact tggtggttca cgggaagacc      60
atactgactg gggttcctga caacattgtg ctgaccccag gatctggcct tggactcgtt     120
```

-continued

```
gctggcgctt tcattggtgc cactgcttcg aacagtaaaa gtctacatgt tttcccagtc      180
ggtgttttag agggtactcg cttcctatgt tgtttccgtt tcaagttatg gtggatgacc      240
caaagaatgg gaacatctgg gagagacatc cctttcgaga cacagttcct gctgatggag      300
agcaagggta acgatggaga ggatcctgat aattcttcga ccatctacac cgtcttcctt      360
cctctccttg agggccagtt ccgtgctgcc ctgcaaggaa atgaaaagaa tgagatggag      420
atttgcctcg agagtggaga taacactgtt gagaccaacc aaggactttc tcttgtctat      480
atgcatgctg gacaaatcc ctttgaagtt atcactcaag cagtgaaggc tgttgaaaag       540
catacgcaaa cttttctaca tagagagaag aaaaagttac cttccttcct tgactggttt      600
ggttggtgta cttgggatgc ttttttacact gatgtcactg ctgagggtgt tgtggaaggt     660
ctcaaaagcc tttcagaggg aggggcacct ccaaagttct taatcataga tgatggttgg      720
caacagatag aagccaaacc aaaagatgct gattgtgttg tacaagaggg agcacagttt      780
gcaagtaggc tgtctggaat aaaagaaaat cataagtttc agaaaaatgg gaataactat      840
gatcaggtcc caggcctaaa ggtggttgtt gatgatgcca agaacaacca caaagtaaaa      900
tttgtgtatg catggcatgc tttggctgga tattggggtg gtgtgaaacc agcaagtcca      960
ggcatggagc attatgattc cgcttttggcg tacccggtcc agtcaccggg tatgttgggc    1020
aaccaaccag acatagttgt agacagcttg gctgttcatg gcattggcct tgtgcatcca    1080
aagaaagtct ttaatttcta taatgagctt cattcctact tggcttcctg tggtatcgat    1140
ggcgtaaagg ttgatgtgca aaacattatt gaaaccctcg gtgctggtca tggtggcagg    1200
gttacactta ctcgtagcta ccatcaggct cttgaagctt cgattgctcg taactttttct   1260 gacaatggat gcattgcttg tatgtgccac aacactgaca gtctctacag tgccaaacag    1320
actgcggtcg tgagagcttc tgatgactat taccctcgtg atcctgcctc ccacaccatt    1380
catatttctt ctgtggctta caattctctt tccttggag agttcatgca gcctgactgg      1440
gatatgttcc atagtttaca tccgacagca gagtatcacg gtgctgctcg tgcaattggc    1500
ggatgtgcaa tttatgtcag tgacaaaacca ggtaaccaca actttgacct gttgaagaaa    1560
ctagtccttc ccgatggatc agttcttcgt gctcagttac ctggccgacc gacacgtgac    1620
tctttgttca cgatccagc tagagatggc accagcctgc tcaaaatttg gaatatgaac     1680
aaatgttctg gtgttgttgg agtattcaat gccaaggtg ccggttggtg caggatcaca     1740
aagaaaactc gcattcacga cgagtctccg ggtacactca ctacgtctgt ccgtgcagct    1800
gatgttgatg ctatttcgca agttgcaggt gccgattgga agggtgatac tattgtttat    1860
gcctatcgat caggggattt gattcgattg ccaaaaggtg cttcagttcc agttaccctc    1920
aaagtcttgg aatatgatct tctccatatt tctcctctga aggacatcgc atcgaacatc    1980
tcatttgcac caattggtct acttgacatg ttcaacaccg tggtgctgt cgaacaagtt    2040 aatgtccaag tggtcgaacc aataccagag ttcgatggtg aagttgcttc tgagctaaca    2100
tgttctctcc ccaatgatcg acctccgaca gctactatca ccatgaaagc ccgaggatgc    2160
agaaggtttg gtctatactc gtcccaacgt cctctgaaat gcagtgtgga caaggtcgat    2220
gtcgactttg tgtacgacga ggtcacaggg ttagtcacct tcgaaattcc tatcccgacg    2280
gaggaaatgt atagatggaa cattgaaatt caagtt                              2316
```

<210> SEQ ID NO 10
<211> LENGTH: 772
<212> TYPE: PRT

<213> ORGANISM: Cucumis melo

<400> SEQUENCE: 10

Met Thr Val Thr Pro Lys Ile Ser Val Asn Asp Gly Asn Leu Val Val
1               5                   10                  15

His Gly Lys Thr Ile Leu Thr Gly Val Pro Asp Asn Ile Val Leu Thr
            20                  25                  30

Pro Gly Ser Gly Leu Gly Leu Val Ala Gly Ala Phe Ile Gly Ala Thr
        35                  40                  45

Ala Ser Asn Ser Lys Ser Leu His Val Phe Pro Val Gly Val Leu Glu
    50                  55                  60

Gly Thr Arg Phe Leu Cys Cys Phe Arg Phe Lys Leu Trp Trp Met Thr
65                  70                  75                  80

Gln Arg Met Gly Thr Ser Gly Arg Asp Ile Pro Phe Glu Thr Gln Phe
                85                  90                  95

Leu Leu Met Glu Ser Lys Gly Asn Asp Gly Glu Asp Pro Asp Asn Ser
            100                 105                 110

Ser Thr Ile Tyr Thr Val Phe Leu Pro Leu Leu Glu Gly Gln Phe Arg
        115                 120                 125

Ala Ala Leu Gln Gly Asn Glu Lys Asn Glu Met Glu Ile Cys Leu Glu
    130                 135                 140

Ser Gly Asp Asn Thr Val Glu Thr Asn Gln Gly Leu Ser Leu Val Tyr
145                 150                 155                 160

Met His Ala Gly Thr Asn Pro Phe Glu Val Ile Thr Gln Ala Val Lys
                165                 170                 175

Ala Val Glu Lys His Thr Gln Thr Phe Leu His Arg Glu Lys Lys Lys
            180                 185                 190

Leu Pro Ser Phe Leu Asp Trp Phe Gly Trp Cys Thr Trp Asp Ala Phe
        195                 200                 205

Tyr Thr Asp Val Thr Ala Glu Gly Val Val Glu Gly Leu Lys Ser Leu
    210                 215                 220

Ser Glu Gly Gly Ala Pro Pro Lys Phe Leu Ile Ile Asp Asp Gly Trp
225                 230                 235                 240

Gln Gln Ile Glu Ala Lys Pro Lys Asp Ala Asp Cys Val Val Gln Glu
                245                 250                 255

Gly Ala Gln Phe Ala Ser Arg Leu Ser Gly Ile Lys Glu Asn His Lys
            260                 265                 270

Phe Gln Lys Asn Gly Asn Asn Tyr Asp Gln Val Pro Gly Leu Lys Val
        275                 280                 285

Val Val Asp Asp Ala Lys Lys Gln His Lys Val Lys Phe Val Tyr Ala
    290                 295                 300

Trp His Ala Leu Ala Gly Tyr Trp Gly Gly Val Lys Pro Ala Ser Pro
305                 310                 315                 320

Gly Met Glu His Tyr Asp Ser Ala Leu Ala Tyr Pro Val Gln Ser Pro
                325                 330                 335

Gly Met Leu Gly Asn Gln Pro Asp Ile Val Val Asp Ser Leu Ala Val
            340                 345                 350

His Gly Ile Gly Leu Val His Pro Lys Lys Val Phe Asn Phe Tyr Asn
        355                 360                 365

Glu Leu His Ser Tyr Leu Ala Ser Cys Gly Ile Asp Gly Val Lys Val
    370                 375                 380

Asp Val Gln Asn Ile Ile Glu Thr Leu Gly Ala Gly His Gly Gly Arg
385                 390                 395                 400

```
Val Thr Leu Thr Arg Ser Tyr His Gln Ala Leu Glu Ala Ser Ile Ala
            405                 410                 415

Arg Asn Phe Ser Asp Asn Gly Cys Ile Ala Cys Met Cys His Asn Thr
            420                 425                 430

Asp Ser Leu Tyr Ser Ala Lys Gln Thr Ala Val Val Arg Ala Ser Asp
            435                 440                 445

Asp Tyr Tyr Pro Arg Asp Pro Ala Ser His Thr Ile His Ile Ser Ser
            450                 455                 460

Val Ala Tyr Asn Ser Leu Phe Leu Gly Glu Phe Met Gln Pro Asp Trp
465                 470                 475                 480

Asp Met Phe His Ser Leu His Pro Thr Ala Glu Tyr His Gly Ala Ala
                485                 490                 495

Arg Ala Ile Gly Gly Cys Ala Ile Tyr Val Ser Asp Lys Pro Gly Asn
            500                 505                 510

His Asn Phe Asp Leu Leu Lys Lys Leu Val Leu Pro Asp Gly Ser Val
            515                 520                 525

Leu Arg Ala Gln Leu Pro Gly Arg Pro Thr Arg Asp Ser Leu Phe Asn
            530                 535                 540

Asp Pro Ala Arg Asp Gly Thr Ser Leu Leu Lys Ile Trp Asn Met Asn
545                 550                 555                 560

Lys Cys Ser Gly Val Val Gly Val Phe Asn Cys Gln Gly Ala Gly Trp
                565                 570                 575

Cys Arg Ile Thr Lys Lys Thr Arg Ile His Asp Glu Ser Pro Gly Thr
            580                 585                 590

Leu Thr Thr Ser Val Arg Ala Ala Asp Val Asp Ala Ile Ser Gln Val
            595                 600                 605

Ala Gly Ala Asp Trp Lys Gly Asp Thr Ile Val Tyr Ala Tyr Arg Ser
610                 615                 620

Gly Asp Leu Ile Arg Leu Pro Lys Gly Ala Ser Val Pro Val Thr Leu
625                 630                 635                 640

Lys Val Leu Glu Tyr Asp Leu Leu His Ile Ser Pro Leu Lys Asp Ile
                645                 650                 655

Ala Ser Asn Ile Ser Phe Ala Pro Ile Gly Leu Leu Asp Met Phe Asn
                660                 665                 670

Thr Gly Gly Ala Val Glu Gln Val Asn Val Gln Val Glu Pro Ile
            675                 680                 685

Pro Glu Phe Asp Gly Glu Val Ala Ser Glu Leu Thr Cys Ser Leu Pro
            690                 695                 700

Asn Asp Arg Pro Pro Thr Ala Thr Ile Thr Met Lys Ala Arg Gly Cys
705                 710                 715                 720

Arg Arg Phe Gly Leu Tyr Ser Ser Gln Arg Pro Leu Lys Cys Ser Val
                725                 730                 735

Asp Lys Val Asp Val Asp Phe Val Tyr Asp Glu Val Thr Gly Leu Val
            740                 745                 750

Thr Phe Glu Ile Pro Ile Pro Thr Glu Glu Met Tyr Arg Trp Asn Ile
            755                 760                 765

Glu Ile Gln Val
    770

<210> SEQ ID NO 11
<211> LENGTH: 3
<212> TYPE: PRT
<213> ORGANISM: Artificial sequence
<220> FEATURE:
<223> OTHER INFORMATION: Box B Conserved motif of the alkaline
``` alpha-galactosidase protein
<220> FEATURE:
<221> NAME/KEY: misc_feature
<222> LOCATION: (2)..(2)
<223> OTHER INFORMATION: Any amino acid

<400> SEQUENCE: 11

Lys Xaa Asp
1

<210> SEQ ID NO 12
<211> LENGTH: 17
<212> TYPE: DNA
<213> ORGANISM: Artificial sequence
<220> FEATURE:
<223> OTHER INFORMATION: Synthetic single strand oligonucleotide
<220> FEATURE:
<221> NAME/KEY: misc_feature
<222> LOCATION: (6)..(6)
<223> OTHER INFORMATION: Any nucleic acid
<220> FEATURE:
<221> NAME/KEY: misc_feature
<222> LOCATION: (9)..(9)
<223> OTHER INFORMATION: Any nucleic acid
<220> FEATURE:
<221> NAME/KEY: misc_feature
<222> LOCATION: (12)..(12)
<223> OTHER INFORMATION: Any nucleic acid

<400> SEQUENCE: 12
acrgtnggng cnggrat                                                17

<210> SEQ ID NO 13
<211> LENGTH: 18
<212> TYPE: DNA
<213> ORGANISM: Artificial sequence
<220> FEATURE:
<223> OTHER INFORMATION: Synthetic single strand oligonucleotide
<220> FEATURE:
<221> NAME/KEY: misc_feature
<222> LOCATION: (1)..(1)
<223> OTHER INFORMATION: Any nucleotide
<220> FEATURE:
<221> NAME/KEY: misc_feature
<222> LOCATION: (7)..(7)
<223> OTHER INFORMATION: modified base: Inosine
<220> FEATURE:
<221> NAME/KEY: misc_feature
<222> LOCATION: (10)..(10)
<223> OTHER INFORMATION: modified base: Inosine

<400> SEQUENCE: 13
nccyaanacn gtyaartt                                               18

<210> SEQ ID NO 14
<211> LENGTH: 51
<212> TYPE: DNA
<213> ORGANISM: Artificial sequence
<220> FEATURE:
<223> OTHER INFORMATION: PCR product, encoding the C. melo N-terminal
      sequence of alkaline-alpha-galactosidase

<400> SEQUENCE: 14
acggttggtg ctggaattac tatctccgat gcgaatttga cggtgttggg a           51

<210> SEQ ID NO 15
<211> LENGTH: 18
<212> TYPE: DNA
<213> ORGANISM: Artificial sequence
<220> FEATURE:
<223> OTHER INFORMATION: Synthetic single strand oligonucleotide

```
<220> FEATURE:
<221> NAME/KEY: misc_feature
<222> LOCATION: (7)..(7)
<223> OTHER INFORMATION: Any nucleotide

<400> SEQUENCE: 15
ytgccanccr tcrtcdat                                                   18

<210> SEQ ID NO 16
<211> LENGTH: 25
<212> TYPE: DNA
<213> ORGANISM: Artificial sequence
<220> FEATURE:
<223> OTHER INFORMATION: Synthetic single strand oligonucleotide

<400> SEQUENCE: 16
aattactatc tccgatgcga atttg                                           25

<210> SEQ ID NO 17
<211> LENGTH: 720
<212> TYPE: DNA
<213> ORGANISM: Artificial sequence
<220> FEATURE:
<223> OTHER INFORMATION: PCR product derived from C. melo

<400> SEQUENCE: 17
aattactatc tccgatgcga atttgacggt gttgggaaat cgtgttttat ccgatgttca     60
taataacatt actctcacgg cggcgccggg tggtggtgtg atgaacggcg ccttcatagg    120
agttcaatct gatcagatcg gtagtcgccg agttttttcct attgggaaat tgatagggtt   180
gagattctta tgtgcttttc gattcaaatt atggtggatg actcaaagaa tggggtgttc    240
cggtcaagaa gttccattcg agacacaatt tcttgtggtg aaacacgtg atggttctaa     300 cattgccgga aatggagagg aaggcgatgc cgtttatact gttttcttc ctattcttga     360 aggcgatttc agagctgttc ttcaagggaa tgataataat gaaattgaaa tctgtttaga    420
aagtggagat ccaagtgtag atgggtttga gggtagccat ttggtgtttg tgggtgctgg    480
atcagatcct tttgaaacca ttacttatgc agtcaagtct gttgaaaagc atttgcaaac    540
ttttgctcat cgcgaaagaa agaagatgcc tgatattttg aactggttcg gctggtgcac    600
atgggatgct ttctacactg atgtcacttc agatggcgtc aagaagggtc ttgaaagctt    660
tgagaatgga ggaattcctc ccaagtttgt cattatcgat gatggatggc aatcagttgc    720

<210> SEQ ID NO 18
<211> LENGTH: 20
<212> TYPE: DNA
<213> ORGANISM: Artificial sequence
<220> FEATURE:
<223> OTHER INFORMATION: Synthetic single strand oligonucleotide
<220> FEATURE:
<221> NAME/KEY: misc_feature
<222> LOCATION: (3)..(3)
<223> OTHER INFORMATION: Modified base: Inosine

<400> SEQUENCE: 18
acngtbggbg cbggbathac                                                 20

<210> SEQ ID NO 19
<211> LENGTH: 17
<212> TYPE: DNA
<213> ORGANISM: Artificial sequence
<220> FEATURE:
<223> OTHER INFORMATION: Synthetic single strand oligonucleotide
<220> FEATURE:
```

```
<221> NAME/KEY: misc_feature
<222> LOCATION: (6)..(6)
<223> OTHER INFORMATION: Any nucleotide
<220> FEATURE:
<221> NAME/KEY: misc_feature
<222> LOCATION: (9)..(9)
<223> OTHER INFORMATION: Any nucleotide
<220> FEATURE:
<221> NAME/KEY: misc_feature
<222> LOCATION: (12)..(12)
<223> OTHER INFORMATION: Any nucleotide

<400> SEQUENCE: 19
acygtnggng cnggyat                                                17

<210> SEQ ID NO 20
<211> LENGTH: 17
<212> TYPE: DNA
<213> ORGANISM: Artificial sequence
<220> FEATURE:
<223> OTHER INFORMATION: Synthetic single strand oligonucleotide
<220> FEATURE:
<221> NAME/KEY: misc_feature
<222> LOCATION: (6)..(6)
<223> OTHER INFORMATION: Any nucleotide
<220> FEATURE:
<221> NAME/KEY: misc_feature
<222> LOCATION: (9)..(9)
<223> OTHER INFORMATION: Any nucleotide
<220> FEATURE:
<221> NAME/KEY: misc_feature
<222> LOCATION: (12)..(12)
<223> OTHER INFORMATION: Any nucleotide

<400> SEQUENCE: 20
acygtnggng cnggrat                                                17

<210> SEQ ID NO 21
<211> LENGTH: 17
<212> TYPE: DNA
<213> ORGANISM: Artificial sequence
<220> FEATURE:
<223> OTHER INFORMATION: Synthetic single strand oligonucleotide
<220> FEATURE:
<221> NAME/KEY: misc_feature
<222> LOCATION: (6)..(6)
<223> OTHER INFORMATION: Any nucleotide
<220> FEATURE:
<221> NAME/KEY: misc_feature
<222> LOCATION: (9)..(9)
<223> OTHER INFORMATION: Any nucleotide
<220> FEATURE:
<221> NAME/KEY: misc_feature
<222> LOCATION: (12)..(12)
<223> OTHER INFORMATION: Any nucleotide

<400> SEQUENCE: 21
acrgtnggng cnggyat                                                17

<210> SEQ ID NO 22
<211> LENGTH: 18
<212> TYPE: DNA
<213> ORGANISM: Artificial sequence
<220> FEATURE:
<223> OTHER INFORMATION: Synthetic single strand oligonucleotide
<220> FEATURE:
<221> NAME/KEY: misc_feature
<222> LOCATION: (1)..(1)
<223> OTHER INFORMATION: Any nucleotide
<220> FEATURE:
<221> NAME/KEY: misc_feature
<222> LOCATION: (4)..(4)
<223> OTHER INFORMATION: Any nucleotide
```

```
<220> FEATURE:
<221> NAME/KEY: misc_feature
<222> LOCATION: (7)..(7)
<223> OTHER INFORMATION: Modified base: Inosine
<220> FEATURE:
<221> NAME/KEY: misc_feature
<222> LOCATION: (10)..(10)
<223> OTHER INFORMATION: Modified base: Inosine
<220> FEATURE:
<221> NAME/KEY: misc_feature
<222> LOCATION: (13)..(13)
<223> OTHER INFORMATION: Any nucleotide

<400> SEQUENCE: 22
nccnagnacn gtnagrtt                                                18

<210> SEQ ID NO 23
<211> LENGTH: 18
<212> TYPE: DNA
<213> ORGANISM: Artificial sequence
<220> FEATURE:
<223> OTHER INFORMATION: Synthetic single strand oligonucleotide
<220> FEATURE:
<221> NAME/KEY: misc_feature
<222> LOCATION: (1)..(1)
<223> OTHER INFORMATION: Any nucleotide
<220> FEATURE:
<221> NAME/KEY: misc_feature
<222> LOCATION: (7)..(7)
<223> OTHER INFORMATION: Modified base: Inosine
<220> FEATURE:
<221> NAME/KEY: misc_feature
<222> LOCATION: (10)..(10)
<223> OTHER INFORMATION: Modified base: Inosine
<220> FEATURE:
<221> NAME/KEY: misc_feature
<222> LOCATION: (13)..(13)
<223> OTHER INFORMATION: Any nucleotide

<400> SEQUENCE: 23
nccyaanacn gtnagrtt                                                18

<210> SEQ ID NO 24
<211> LENGTH: 18
<212> TYPE: DNA
<213> ORGANISM: Artificial sequence
<220> FEATURE:
<223> OTHER INFORMATION: Synthetic single strand oligonucleotide
<220> FEATURE:
<221> NAME/KEY: misc_feature
<222> LOCATION: (1)..(1)
<223> OTHER INFORMATION: Any nucleotide
<220> FEATURE:
<221> NAME/KEY: misc_feature
<222> LOCATION: (4)..(4)
<223> OTHER INFORMATION: Any nucleotide
<220> FEATURE:
<221> NAME/KEY: misc_feature
<222> LOCATION: (7)..(7)
<223> OTHER INFORMATION: Modified base: Inosine
<220> FEATURE:
<221> NAME/KEY: misc_feature
<222> LOCATION: (10)..(10)
<223> OTHER INFORMATION: Modified base: Inosine

<400> SEQUENCE: 24
nccnagnacn gtyaartt                                                18

<210> SEQ ID NO 25
<211> LENGTH: 22
<212> TYPE: DNA
<213> ORGANISM: Artificial sequence
<220> FEATURE:
```

<223> OTHER INFORMATION: Synthetic single strand oligonucleotide

<400> SEQUENCE: 25
gtgggtgctg gatcagatcc tt                                          22

<210> SEQ ID NO 26
<211> LENGTH: 25
<212> TYPE: DNA
<213> ORGANISM: Artificial sequence
<220> FEATURE:
<223> OTHER INFORMATION: Synthetic single strand oligonucleotide

<400> SEQUENCE: 26
accattactt atgcagtcaa gtctg                                       25

<210> SEQ ID NO 27
<211> LENGTH: 1956
<212> TYPE: DNA
<213> ORGANISM: Artificial sequence
<220> FEATURE:
<223> OTHER INFORMATION: RACE product derived from C. melo

<400> SEQUENCE: 27

```
accattactt atgcagtcaa gtctgttgaa aagcatttgc aaacttttgc tcatcgcgaa    60
agaaagaaga tgcctgatat tttgaactgg ttcggctggt gcacatggga tgctttctac   120
actgatgtca cttcagatgg cgtcaagaag ggtcttgaaa gctttgagaa tggaggaatt   180
cctcccaagt ttgtcattat cgatgatgga tggcaatcag ttgccaagga tgctactagt   240
gctgattgca aagctgataa cacagcaaac tttgcaaaca ggttaactca cataaaagag   300
aattacaaat ttcaaaaaga tggcaaagag ggtgaaagaa ttgagaaccc tgcactgggt   360
cttcaacata ttgtgtccta catgaaagag aagcatgcga ccaagtatgt ttatgtttgg   420
catgccataa caggctactg gggtggtgtg agtgctggag ttaaagagat ggaacaatat   480
gagtccaaga ttgcgtaccc ggttgcatct cctggggtcg aatcaaatga gccatgtgat   540
gctttgaata gcatcaccaa aactggactt ggccttgtga ccctgaaaaa ggttttcaac   600
ttctacaatg aacaacactc gtatcttgcg tctgctggtg ttgatggagt taagttgat    660
gttcaaaaca ttcttgagac gcttggagca ggtcatggtg aaagagttaa acttgctaga   720
aaataccatc aggctcttga ggcatcgatt tcccgaaact ttcaagataa cggaatcatt   780
tcgtgtatga gtcataatac cgatggttta tacagttcaa agagaaatgc tgttattcga   840
gcatcggatg attttggcc tagagatcca gcatctcaca cgattcatat agcatcagtt   900
gcttacaact cctattttct tggggagttt atgcagccag attgggatat gtttcatagt   960
cttcatccta tggccgaata tcacggagca gctcgtgccg tgggaggatg tgctatatat  1020
gtcagtgaca agcctggtca acatgacttc aatcttttga agaagcttgt cctccctgat  1080
ggttctattc tgagagctaa gctccccgga cggccgacaa aggactgcct atttacggat  1140
cctgctagag atggaaaaag tctattgaag atttggaatt tgaatgatct atctggagtt  1200
gttgggtct ttaactgcca aggagcagga tggtgtaagg ttggaaagaa aaacctcatt   1260
cacgacgaga atccagacac gatcacgggg gttattcgag caaaagatgt tagttatcta  1320
tggaagattg caggcgagtc ctggacaggg gatgcagtga tattctccca tcttgctgga  1380
gaagttgttt acctgccaca agatgcatcg atgccaataa ccttgaagcc tcgagagttc  1440
gacgtcttca cggttgttcc tgtcaaggaa ctagttaatg acatcaagtt tgctcctata  1500
ggtttgatca agatgttcaa ctctggagga gcagtgaaag aaatgaacca tcaacctgga  1560
```

```
agttcgaatg tgtcgctgaa agttcggggt tctgggccat tcggggcata ttcctcgagc      1620
aaaccgaagc gtgtagcagt cgactcggag gaggtagagt tcatgtatga tgagggtggt      1680
ttaatcacca ttgacttgaa ggtaccagag aaagagttgt acctttggga tataagaatt      1740
gaactatgag aacaaaatta gaaaacaat gattcttttc ttgaatattt ctgagaattt       1800
ggatggatgg gaaatattct ttcctatatg attttttttc cattatgtaa ctcctcttgt      1860
aaacccattt aataatggga ataaaataat tttaataaaa ttaaaccaca ctcttagttt      1920
gagttattaa aaaaaaaaaa aaaaaaaaaa aaaaaa                                1956

<210> SEQ ID NO 28
<211> LENGTH: 33
<212> TYPE: DNA
<213> ORGANISM: Artificial sequence
<220> FEATURE:
<223> OTHER INFORMATION: Synthetic single strand oligonucleotide

<400> SEQUENCE: 28
atgacggttg gtgctggaat tactatctcc gat                                   33

<210> SEQ ID NO 29
<211> LENGTH: 36
<212> TYPE: DNA
<213> ORGANISM: Artificial sequence
<220> FEATURE:
<223> OTHER INFORMATION: Synthetic single strand oligonucleotide

<400> SEQUENCE: 29
tcatagttca attcttatat cccaaaggta gaactc                                36

<210> SEQ ID NO 30
<211> LENGTH: 17
<212> TYPE: DNA
<213> ORGANISM: Artificial sequence
<220> FEATURE:
<223> OTHER INFORMATION: Synthetic single strand oligonucleotide
<220> FEATURE:
<221> NAME/KEY: misc_feature
<222> LOCATION: (12)..(12)
<223> OTHER INFORMATION: Any nucleotide

<400> SEQUENCE: 30
tggtggatga cncarmg                                                     17

<210> SEQ ID NO 31
<211> LENGTH: 17
<212> TYPE: DNA
<213> ORGANISM: Artificial sequence
<220> FEATURE:
<223> OTHER INFORMATION: Synthetic single strand oligonucleotide
<220> FEATURE:
<221> NAME/KEY: misc_feature
<222> LOCATION: (9)..(9)
<223> OTHER INFORMATION: Any nucleotide

<400> SEQUENCE: 31
gcrtcccang tmcacca                                                     17

<210> SEQ ID NO 32
<211> LENGTH: 6
<212> TYPE: PRT
<213> ORGANISM: Artificial sequence
<220> FEATURE:
<223> OTHER INFORMATION: Conserved amino acid sequence derived from C.
      melo alpha-galactosidase protein
```

```
<400> SEQUENCE: 32

Trp Trp Met Thr Gln Arg
1               5

<210> SEQ ID NO 33
<211> LENGTH: 6
<212> TYPE: PRT
<213> ORGANISM: Artificial sequence
<220> FEATURE:
<223> OTHER INFORMATION: Conserved amino acid sequence derived from C.
      melo alpha-galactosidase protein

<400> SEQUENCE: 33

Trp Cys Thr Trp Asp Ala
1               5

<210> SEQ ID NO 34
<211> LENGTH: 393
<212> TYPE: DNA
<213> ORGANISM: Artificial sequence
<220> FEATURE:
<223> OTHER INFORMATION: PCR product derived from C. melo

<400> SEQUENCE: 34
tggtggatga cccaaagaat gggaacatct gggagagaca tcccttttcga gacacagttc      60 ctgctgatgg agagcaaggg taacgatgga gaggatcctg ataattcttc gaccatctac     120
accgtcttcc ttcctctcct tgagggccag ttccgtgctg ccctgcaagg aaatgaaaag     180
aatgagatgg agatttgcct cgagagtgga gataacactg ttgagaccaa ccaaggactt     240
tctcttgtct atatgcatgc tgggacaaat ccctttgaag ttatcactca agcagtgaag     300
gctgttgaaa agcatacgca aacttttcta catagagaga agaaaaagtt accttccttc     360
cttgactggt tggttggtg tacttgggat gct                                    393

<210> SEQ ID NO 35
<211> LENGTH: 23
<212> TYPE: DNA
<213> ORGANISM: Artificial sequence
<220> FEATURE:
<223> OTHER INFORMATION: Synthetic single strand oligonucleotide

<400> SEQUENCE: 35
ggagagcaag ggtaacgatg gag                                               23

<210> SEQ ID NO 36
<211> LENGTH: 25
<212> TYPE: DNA
<213> ORGANISM: Artificial sequence
<220> FEATURE:
<223> OTHER INFORMATION: Synthetic single strand oligonucleotide

<400> SEQUENCE: 36
acgagtaagt gtaaccctgc cactg                                             25

<210> SEQ ID NO 37
<211> LENGTH: 26
<212> TYPE: DNA
<213> ORGANISM: Artificial sequence
<220> FEATURE:
<223> OTHER INFORMATION: Synthetic single strand oligonucleotide

<400> SEQUENCE: 37
atgacggtca caccgaaaat ttctgt                                            26
```

<210> SEQ ID NO 38
<211> LENGTH: 26
<212> TYPE: DNA
<213> ORGANISM: Artificial sequence
<220> FEATURE:
<223> OTHER INFORMATION: Synthetic single strand oligonucleotide

<400> SEQUENCE: 38
gcctccacca tacacattca ttgctc                                        26

<210> SEQ ID NO 39
<211> LENGTH: 33
<212> TYPE: DNA
<213> ORGANISM: Artificial sequence
<220> FEATURE:
<223> OTHER INFORMATION: Synthetic single strand oligonucleotide

<400> SEQUENCE: 39
atgacggttg gtgctggaat tactatctcc gat                                33

<210> SEQ ID NO 40
<211> LENGTH: 36
<212> TYPE: DNA
<213> ORGANISM: Artificial sequence
<220> FEATURE:
<223> OTHER INFORMATION: Synthetic single strand oligonucleotide

<400> SEQUENCE: 40
tcatagttca attcttatat cccaaaggta gaactc                             36

<210> SEQ ID NO 41
<211> LENGTH: 26
<212> TYPE: DNA
<213> ORGANISM: Artificial sequence
<220> FEATURE:
<223> OTHER INFORMATION: Synthetic single strand oligonucleotide

<400> SEQUENCE: 41
atgacggtca caccgaaaat ttctgt                                        26

<210> SEQ ID NO 42
<211> LENGTH: 26
<212> TYPE: DNA
<213> ORGANISM: Artificial sequence
<220> FEATURE:
<223> OTHER INFORMATION: Synthetic single strand oligonucleotide

<400> SEQUENCE: 42
gcctccacca tacacattca ttgctc                                        26

<210> SEQ ID NO 43
<211> LENGTH: 24
<212> TYPE: DNA
<213> ORGANISM: Artificial sequence
<220> FEATURE:
<223> OTHER INFORMATION: Synthetic single strand oligonucleotide

<400> SEQUENCE: 43
cagatcggta gtcgccgagt tttt                                          24

<210> SEQ ID NO 44
<211> LENGTH: 24
<212> TYPE: DNA
<213> ORGANISM: Artificial sequence
<220> FEATURE:

-continued

<223> OTHER INFORMATION: Synthetic single strand oligonucleotide

<400> SEQUENCE: 44
aacagtaaaa gtctacatgt tttc                                          24

<210> SEQ ID NO 45
<211> LENGTH: 9
<212> TYPE: PRT
<213> ORGANISM: Artificial sequence
<220> FEATURE:
<223> OTHER INFORMATION: Conserved motif in seed imbibition protein
      (SIP) family
<220> FEATURE:
<221> NAME/KEY: misc_feature
<222> LOCATION: (6)..(6)
<223> OTHER INFORMATION: Phenylalanine or Tyrosine
<220> FEATURE:
<221> NAME/KEY: misc_feature
<222> LOCATION: (7)..(7)
<223> OTHER INFORMATION: Tryptophan or Tyrosine

<400> SEQUENCE: 45

Arg Ala Ser Asp Asp Xaa Xaa Pro Arg
1               5

<210> SEQ ID NO 46
<211> LENGTH: 19
<212> TYPE: PRT
<213> ORGANISM: Artificial sequence
<220> FEATURE:
<223> OTHER INFORMATION: Conserved motif in seed imbibition protein
      (SIP) family

<400> SEQUENCE: 46

Leu Phe Leu Gly Glu Phe Met Gln Pro Asp Trp Asp Met Phe His Ser
1               5                   10                  15

Leu His Pro

<210> SEQ ID NO 47
<211> LENGTH: 8
<212> TYPE: PRT
<213> ORGANISM: Artificial sequence
<220> FEATURE:
<223> OTHER INFORMATION: Conserved motif in seed imbibition protein
      (SIP) family

<400> SEQUENCE: 47

Ile Tyr Val Ser Asp Lys Pro Gly
1               5

<210> SEQ ID NO 48
<211> LENGTH: 16
<212> TYPE: PRT
<213> ORGANISM: Artificial sequence
<220> FEATURE:
<223> OTHER INFORMATION: Conserved motif in seed imbibition protein
      (SIP) family
<220> FEATURE:
<221> NAME/KEY: misc_feature
<222> LOCATION: (4)..(4)
<223> OTHER INFORMATION: Iso-leucine or Valine
<220> FEATURE:
<221> NAME/KEY: misc_feature
<222> LOCATION: (8)..(8)
<223> OTHER INFORMATION: Any amino acid
<220> FEATURE:
<221> NAME/KEY: misc_feature
<222> LOCATION: (15)..(15)
<223> OTHER INFORMATION: Any amino acid -continued

```
<400> SEQUENCE: 48

Asp Gly Ser Xaa Leu Arg Ala Xaa Leu Pro Gly Arg Pro Thr Xaa Asp
1               5                   10                  15

<210> SEQ ID NO 49
<211> LENGTH: 6
<212> TYPE: PRT
<213> ORGANISM: Artificial sequence
<220> FEATURE:
<223> OTHER INFORMATION: Conserved motif in seed imbibition protein
      (SIP) family

<400> SEQUENCE: 49

Ile Asp Asp Gly Trp Gln
1               5
```

POLYNUCLEOTIDE SEQUENCES ENCODING ALKALINE α-GALACTOSIDASES AND METHODS OF USING SAME

CROSS-REFERENCE TO RELATED APPLICATIONS

This application is a continuation of International application PCT/IL03/00392 filed May 15, 2003 and claims the benefit of U.S. provisional application 60/380,254 filed May 15, 2002, the entire contents of each of which are expressly incorporated herein by reference thereto.

FIELD AND BACKGROUND OF THE INVENTION

The present invention is of polynucleotide sequences encoding alkaline-α-galactosidases and methods of using same.

The α-galactosidase enzyme (α-D-galactoside galactohydrolase) catalyzes the hydrolysis of the terminal linked α-galactose moiety from galactose-containing oligosaccharides. These include, for example, the naturally occurring disaccharide melibiose (6-O-α-D-galactopyranosyl-D-glucose), the trisaccharide raffinose (O-α-D-galactopyranosyl-(1-6)-O-α-D-glucopyranosyl-(1-2)-beta-D-fructofuranoside) and the tetrasaccharide stachyose (O-α-D-galactopyranosyl-(1-6)-O-α-D-galactopyranosyl-(1-6)-O-α-D-glucopyranosyl-(1-2)-beta-D-fructofuranoside).

α-galactosidases are classified into two families of the glycosyl hydrolase enzymes, with eukaryotic enzymes falling primarily into family 27 and prokaryotic enzymes primarily into family 36 [Henrissat A. et al. (1995) Biochem. J. 311:351-352 and Henrissat A. et al. (1991) Biochem. J. 280:309-316]. The α-galactosidases are also classified as acid or alkaline, depending on the pH of optimal activity. Most of the eukaryotic α-galactosidases studied to date are acidic α-galactosidases, with a broad pH optima in the acidic range [Keller F. and Pharr D. M. In: Zamski, E. and Schaffer, A. A. (eds.) Photoassimilate Partitioning in Plants and Crops: Source-Sink Relationships, ch. 7, pp. 168-171, 1996, Marcel Dekker Publ., N.Y.].

α-galactosidases have potential use in a variety of applications. [Margolles-Clark et al. (1996) Eur. J. Biochemistry, 240:104-111 and U.S. Pat. Nos. 5,633,130, 6,197,566 and 5,919,690 each of which is herein incorporated by reference in its entirety]; They may hydrolyze α-galactose residues from polymeric galactomannans, such as in guar gum, where modification of guar gum galactomannan with α-galactosidase has been used to improve the gelling properties of the polysaccharide [Bulpin, P. V., et al (1990) Carbohydrate Polymers 12:155-168]; α-galactosidase can hydrolyze raffinose from beet sugar syrup, which can be used to facilitate the sugar crystallization from molasses [Suzuki et al(1969) Agr. Biol. Chem., 33:501-513].

Additionally, α-galactosidases can also be used to hydrolyze stachyose and raffinose in soybean milk, thereby reducing or eliminating the undesirable digestive side effects which are associated with soybean milk [Thananunkul et al. (1976) Jour. Food Science, 41:173-175) and to remove the terminal α-galactose residue from other glycans, such as the erythrocyte surface antigen conferring blood group B specificity which has potential medical use in transfusion therapy by converting blood group type B to universal donor type O [Harpaz et al.(1975) Archives of Biochemistry and Biophysics, 170:676-683; and Zhu et al. (1996) Archives of Biochemistry and Biophysics, 327:324-329].

However, the use of acidic α-galactosidases in biotechnological and industrial applications is limited by the pH needed for activity. For instance, the use of an acidic form of α-galactosidase to remove the galactose-containing oligosaccharides, which include raffinose and stachyose, from soybean milk is difficult, as the pH of soybean milk, which is 6.2-6.4, is well above the optimum pH range of the *Mortariella vinacea* enzyme, which is 4.0-4.5, as shown using the natural substrate melibiose. Lowering the pH of the soybean milk solution to conform to the acidic pH optimum of this enzyme causes the soybean proteins to precipitate thus imparting a sour taste to the milk [Thanaunkul et al. (1976) Jour. Food Science, 41:173-175, 1976].

Likewise, use of α-galactosidase with an acidic pH optimum for the removal of raffinose from beet sugar faces a similar problem. The pH of the beet molasses has to be lowered to 5.2 with sulfuric acid in order for the *Mortariella vinacea* enzyme to function [Suzuki et al. (1969) Agr. Biol. Chem., 33:501-513].

The standard procedure for seroconversion requires the transfer of centrifuged erythrocytes to an acidic buffer in order for the acidic enzyme to function [Goldstein et al. (1982) Science 215:168-170, 1982]. However, lowering the pH for optimal activity of the coffee bean α-galactosidase causes the cells to be less stable thereby leading to cell lysis. Thus, seroconversion is carried out at pH 5.6, which reflects a compromise between red cell viability and optimal α-galactosidase activity [Zhu et al. (1996) Archives of Biochemistry and Biophysics, 327:324-329].

An additional limitation facing industrial application of α-galactosidases is that the product of the reaction, namely galactose, frequently inhibits their activity. For example, the reported alkaline α-galactosidase from *Cucurbita pepo* leaves is strongly inhibited by α-galactose [Geaudreault, P. R. and Webb, J. A. (1983) Plant Physiol., 71, 662-668].

Despite their importance in various commercial applications, only a few examples of eukaryotic alkaline α-galactosidases have been reported.

A plant alkaline-α-galactosidase with pH optima of 7-7.5 was initially discovered in young leaves of *Cucurbita pepo* [Gaudreault and Webb (1982) Plant Sci. Lett. 24:281-288, (1983) Plant Physiol. 71:662-668 and (1986) Plant Science 45:71-75]. This alkaline form has been reported to be stachyose specific, with only low affinity for raffinose and melibiose. Thus, this previously reported alkaline α-galactosidase could be described as having activity at alkaline pH but with only a narrow spectrum of substrates. Further characterization showed that α-D-galactose, the product of the enzymatic reaction, is a strong inhibitor of the enzyme's activity [Gaudreault and Webb (1983) Plant Physiol. 71:662-668], similar to many of the acid α-galactosidases.

It has been suggested that the alkaline-α-galactosidase from young leaves of cucurbit plays an important physiological role in phloem unloading and catabolism of transported stachyose in the young cucurbit leaf tissue, as it is the initial enzyme in the metabolic pathway of stachyose and raffinose catabolism. Likewise, it has been suggested that the enzyme may play an important role in the carbohydrate partitioning in melon plants, and may have possible functions for phloem unloading in fruits of muskmelon [Gaudreault P R and Webb J A (1986) Plant Science 45:71-75].

Recently, α-galactosidase activity at alkaline pH has been observed in other cucurbit tissue, such as cucumber fruit pedicels, young squash fruit and young melon fruit [Pharr and Hubbard (1994) Encyclopedia of Agricultural Science vol. 3 pp. 25-37]. All these observations suggest that stachyose degradation by α-galactosidase take place within pedicels of fruit of Cucumis sativus, especially in the regions where the pedicel joins the fruit.

A major reservation to the above described alkaline activity stems from the fact that all of these studies were carried out using the non-specific artificial substrate, p-nitrophenyl α-galactopyranoside (pNPG), which indicates α-galactosidase activity but does not reflect either the physiological role of the particular enzyme form, or, more importantly, the substrate specificity of the particular enzyme. Since it is well established that the artificial substrate pNPG often indicates a higher pH optimum for α-galactosidase activity than that observed with the natural substrates [Courtois and Petek (1966) Methods in Enzymology 8:565-571], the prior art does not teach the exact nature of the in-vivo activity of the above described alkaline α-galactosidase enzyme.

Alkaline α-galactosidase activity has been recently reported in plant families other than the Cucurbit family [Bachmann et al. Plant Physiology 105:1335-1345, 1994]. Though these are only very preliminary results accompanied by limited biochemical data, it indicates the possibility that alkaline α-galactosidases, including novel enzymes not previously characterized, may function throughout the plant kingdom.

While reducing the present invention to practice the present inventors have cloned two novel alkaline-α-galactosidase genes, which represent a previously unidentified glycosyl hydrolase family of alkaline-α-galactosidase which is similar to the yet uncharacterized seed imbibition protein (SIP) family.

Further characterization of these genes and their protein products has revealed that the enzymes of the present inventions have optimal activity at neutral to alkaline pH conditions (7-9) together with broad substrate specificity, as opposed to previously reported alkaline-α-galactosidases Thus, the present invention provides novel polynucleotide sequences encoding alkaline-α-galactosidases and methods of using same for producing recombinant proteins, for determining the germination potential of seeds as well as other applications.

SUMMARY OF THE INVENTION

According to one aspect of the present invention there is provided an isolated nucleic acid comprising a genomic, complementary or composite polynucleotide sequence encoding a polypeptide at least 79% homologous to SEQ ID NO: 6, as determined using the BestFit software of the Wisconsin sequence analysis package, utilizing the Smith and Waterman algorithm, where the gap creation equals 8 and gap extension penalty equals 2.

According to yet another aspect of the present invention there is provided an isolated nucleic acid comprising a genomic, complementary or composite polynucleotide sequence encoding a polypeptide at least 82% homologous to SEQ ID NO: 10, as determined using the BestFit software of the Wisconsin sequence analysis package, utilizing the Smith and Waterman algorithm, where the gap creation equals 8 and gap extension penalty equals 2.

According to still another aspect of the present invention there is provided an isolated nucleic acid comprising a genomic, complementary or composite polynucleotide sequence hybridizable with SEQ ID NO: 5 under moderate hybridization conditions by hybridization solution containing 10% dextrane sulfate, 1 M NaCl, 1% SDS and $5 \times 10^6$ cpm $^{32}$P labeled probe, at 65° C., with a final wash solution of 1×SSC and 0.1% SDS and final wash at 50° C.

According to an additional aspect of the present invention there is provided an isolated nucleic acid comprising a genomic, complementary or composite polynucleotide sequence hybridizable with SEQ ID NO: 9 under moderate hybridization conditions by hybridization solution containing 10% dextrane sulfate, 1 M NaCl, 1% SDS and $5 \times 10^6$ cpm $^{32}$P labeled probe, at 65° C., with a final wash solution of 1×SSC and 0.1% SDS and final wash at 50° C.

According to yet an additional aspect of the present invention there is provided an isolated nucleic acid comprising a genomic, complementary or composite polynucleotide sequence at least 84% identical with SEQ ID NO: 5 as determined using the BestFit software of the Wisconsin sequence analysis package, utilizing the Smith and Waterman algorithm, where gap weight equals 50, length weight equals 3, average match equals 10 and average mismatch equals −9.

According to still an additional aspect of the present invention there is provided an isolated nucleic acid comprising a genomic, complementary or composite polynucleotide sequence at least 85% identical with SEQ ID NO: 9 as determined using the BestFit software of the Wisconsin sequence analysis package, utilizing the Smith and Waterman algorithm, where gap weight equals 50, length weight equals 3, average match equals 10 and average mismatch equals −9.

According to a further aspect of the present invention there is provided an isolated nucleic acid comprising a polynucleotide sequence as set forth in SEQ ID NO: 5 or 9 or active portions thereof.

According to yet a further aspect of the present invention there is provided an oligonucleotide of at least 17 bases specifically hybridizable with an isolated nucleic acids set forth in SEQ ID NO: 5 or 9.

According to still a further aspect of the present invention there is provided a pair of oligonucleotides each of at least 17 bases specifically hybridizable with SEQ ID NO: 5 or 9 in an opposite orientation so as to direct specific exponential amplification of a portion thereof in a nucleic acid amplification reaction.

According to a supplementary aspect of the present invention there is provided an antibody or fragment thereof capable of specifically binding a polypeptide including an amino acid sequence selected from the group consisting of SEQ ID NOs: 4, 7 8 and 45-48 the polypeptide having an alkaline-α-galactosidase activity.

According to yet a supplementary aspect of the present invention there is provided a method of producing a recombinant alkaline-α-galactosidase protein, the method comprising: (a) introducing into a cell an expression construct encoding a polypeptide, wherein the polypeptide includes an amino acid sequence selected from the group consisting of SEQ ID NOs: 4, 7 8 and 45-48 and whereas the polypeptide has an alkaline-α-galactosidase activity; (b) culturing the cell under effective conditions which allow expression of the polypeptide; and (c) recovering the polypeptide from the cell culture, thereby producing the recombinant alkaline-α-galactosidase protein.

According to yet a supplementary aspect of the present invention there is provided a method of determining the germination potential of seeds, the method comprising analyzing the seeds for activity or expression level of an alkaline-α-galactosidase including the amino acid sequence selected from the group consisting of SEQ ID NOs: 4, 7 8 and 45-48, the activity or expression levels being indicative of the germination potential of the seeds.

According to an added aspect of the present invention there is provided a method of identifying an alkaline-α-galactosidase, the method comprising: (a) isolating polynucleotide sequences encoding polypeptides including the amino acid sequence selected from the group consisting of SEQ ID NOs: 4, 7 8 and 45-48; (b) expressing the polypeptides; and (c) selecting from the expressed polypeptides a polypeptide exhibiting α-galactosidase activity under alkaline pH conditions, thereby identifying the alkaline-α-galactosidase.

According to further features of this aspect of the present invention the step of expressing the polypeptides is effected in-vivo.

According to further features of this aspect of the present invention the step of expressing the polypeptides is effected in-vitro.

According to yet an added aspect of the present invention there is provided an isolated polypeptide at least 82% homologous to SEQ ID NO: 10, as determined using the BestFit software of the Wisconsin sequence analysis package, utilizing the Smith and Waterman algorithm, where the gap creation equals 8 and gap extension penalty equals 2.

According to further features of this aspect of the present invention the isolated polypeptide sequence is as set forth in SEQ ID NO: 10 or active portions thereof.

According to yet an added aspect of the present invention there is provided a method of removing α-galactose from galactosyl-saccharide containing sample, the method comprising contacting the sample with a composition including, as an active agent, an isolated polypeptide at least 82% homologous to SEQ ID NO: 10, as determined using the BestFit software of the Wisconsin sequence analysis package, utilizing the Smith and Waterman algorithm, where the gap creation equals 8 and gap extension penalty equals 2 so as to remove α-galactose from the galactosyl-saccharide containing sample.

According to still an added aspect of the present invention there is provided a method of seroconverting blood type B erythrocytes to blood type O erythrocytes, the method comprising contacting the blood type B erthrocytes with a composition including, as an active agent, an isolated polypeptide at least 82% homologous to SEQ ID NO: 10, as determined using the BestFit software of the Wisconsin sequence analysis package, utilizing the Smith and Waterman algorithm, where the gap creation equals 8 and gap extension penalty equals 2 so as to remove the terminal α-linked from group B surface antigen of the blood type B erythrocytes thereby seroconverting the blood type B erythrocytes to the blood type O erythrocytes.

According to an other aspect of the present invention there is provided a method of facilitating crystallization of sugar beet sucrose from sugar beet molasses, the method comprising contacting the sugar beet molasses with a composition including, as an active agent, an isolated polypeptide at least 82% homologous to SEQ ID NO: 10, as determined using the BestFit software of the Wisconsin sequence analysis package, utilizing the Smith and Waterman algorithm, where the gap creation equals 8 and gap extension penalty equals 2, so as to hydrolyze raffinose in the molasses to galactose and sucrose, thereby facilitating the crystallization of the sugar beet sucrose from the sugar beet molasses.

According to yet an other aspect of the present invention there is provided a method of reducing the capability of foodstuff to cause digestion associated flatulence the method comprising contacting the foodstuff with a composition including, as an active agent, an isolated polypeptide at least 82% homologous to SEQ ID NO: 10, as determined using the BestFit software of the Wisconsin sequence analysis package, utilizing the Smith and Waterman algorithm, where the gap creation equals 8 and gap extension penalty equals 2, so as to hydrolyze α-galactosyl saccharide contained in the foodstuff, thereby reducing the capability of foodstuff to cause digestion associated flatulence.

According to still an other aspect of the present invention there is provided a method of modifying the rheological properties of an α-galactosyl saccharide containing plant gum, the method comprising contacting the plant gum with a composition including, as an active agent, an isolated polypeptide at least 82% homologous to SEQ ID NO: 10, as determined using the BestFit software of the Wisconsin sequence analysis package, utilizing the Smith and Waterman algorithm, where the gap creation equals 8 and gap extension penalty equals 2, so as to hydrolyze α-galactosyl saccharide contained in the plant gum, thereby modifying the rheological properties of the α-galactosyl saccharide containing plant gum.

The present invention successfully addresses the shortcomings of the presently known configurations by providing polynucleotide sequences encoding alkaline-α-galactosidases and methods of using same.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-d illustrate the nucleotide sequences (SEQ ID NO: 5 and 9, FIG. 1a and FIG. 1c) and deduced amino acid sequences (SEQ ID NO: 6 and 10, FIG. 1b and FIG. 1d) of C. melo alkaline-α-galactosidase I and II genes, respectively.

FIG. 2 is a multiple sequence alignment depicting homology between the Aga-I and Aga-II genes of the present invention and the multigene families of SIP and RFO. Abbreviations, Accession numbers and SEQ ID numbers are as follows: Cucumis melo alkaline-α-galactosidase I, (Cuc mel Aga-I)-SEQ ID NO: 6; Cucumis melo alkaline-α-galactosidase II, (Cuc mel Aga-II)-SEQ ID NO: 10; SIP family GenBank Accession Nos: Arabidopsis thaliana (At NP_175970)-SEQ ID NO: 50, Arabidopsis thaliana (At CAB66109)-SEQ ID NO: 51, Brassica oleracea (Bo X79330)-SEQ ID NO: 52 , Persea americana (Pa_CAB77245)-SEQ ID NO: 53, Hordeum vulgare (Hv S27762)-SEQ ID NO: 54; RFO family GenBank Accession Nos: Pisum sativum stachyose synthase (Ps CAC38094)-SEQ ID NO: 55, Vigna angularis stachyose synthase (Va CAB64363)-SEQ ID NO: 56, Arabidopsis thaliana RFO synthase(At_AAD22659)-SEQ ID NO: 57, Arabidopsis thaliana raffinose synthase (At BAB11595)-SEQ ID NO: 58 and Cucumis sativus raffinose synthase (CsE 15707)-SEQ ID NO: 59. Asterisks below the 7 Aga/SIP sequences indicate conserved amino acids among these 7 sequences. Asterisks below the five RFO synthase sequences indicate conserved amino acids among all twelve Aga/SIP/RFOsynthases. Highlighting indicates examples of unique amino acid sequences within the Aga/SIP family that can be used to distinguish from the RFO synthases.

FIG. 7 shows amino acid sequence conservation between phylogenetically distinct families of α-galactosidases. A and B indicate conserved domains. Characters below indicate conserved amino acids.

Figure 3:
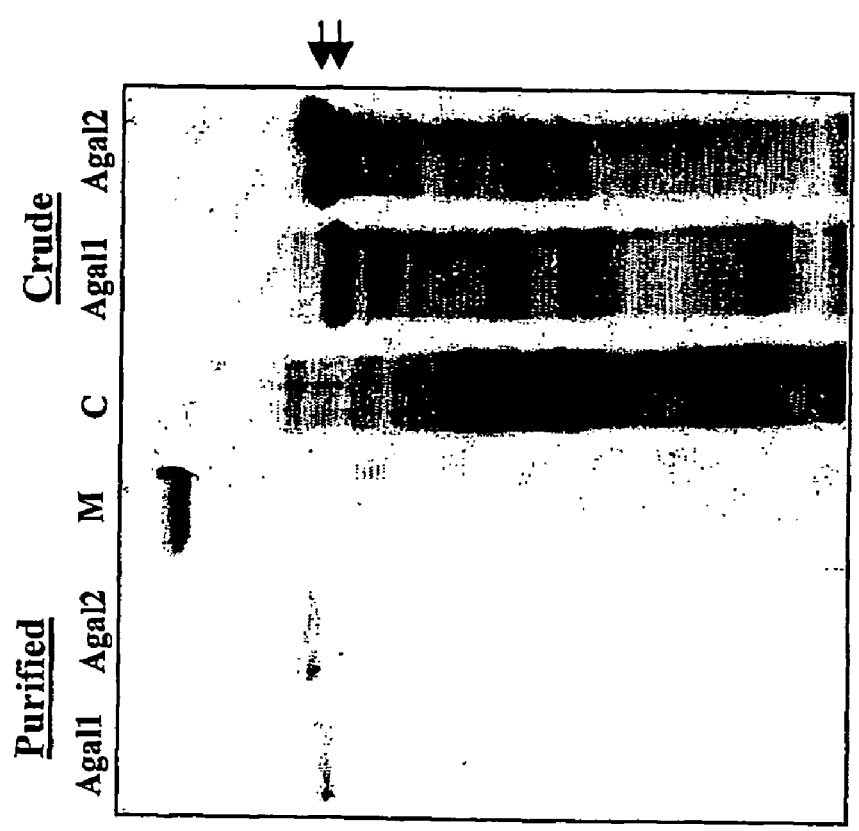
FIG. 3 shows expression of recombinant Aga-I and Aga-II. Protease-defficient E.coli BL21 (DE3) LysE cells [Dubendorff J W and Studier F W (1991). "Controlling basal expression in inducible T7 expression system by blocking the target T7 promoter with lac repressor." J. Mol. Biol. 219: 45-59] were transformed with bacterial expression vectors encoding Histidine-tagged Aga-I and Aga-II proteins, as well as with control empty vector (c). Tagged proteins from IPTG induced bacterial cell extracts, were purified on Nickel columns and analyzed on SDS-PAGE. Proteins were visualized with Coomassie Blue staining. Lanes 1-3 show Aga expression in crude protein extracts. Lanes 5-6 show histidine-tagged proteins following purification. Arrows indicate Aga gene products in both crude extracts and following purification.

RFO family GenBank Accession Nos and Abbreviations:
   *Cucumis melo* alkaline-α-galactosidase II, (Cuc mel Aga-II)-SEQ ID NO: 10; vulgare (Hv S27762)-SEQ ID NO: 54; *Cucumis melo* alkaline-α-galactosidase I, (Cuc mel Aga-I)-SEQ ID NO: 6; *Cucumis sativus* raffinose synthase (CsE 15707)-SEQ ID NO: 59, *Pisum sativum* stachyose synthase (Ps CAC38094)-SEQ ID NO: 55;

FAMILY 27 GenBank Accession Nos and Abbreviations:
   *Coffea Arabica* Alpha-galactosidase (Q42656)-SEQ ID NO: 60; *Cyamopsis tetragonoloba* Alpha-galactosidase (P14749) SEQ ID NO: 61; *A. thaliana* alpha-galactosidase (NP_91190) SEQ ID NO: 62; *Aspergillus niger* alpha-galactosidase aglB (XP_001400244) SEQ ID NO: 63; *Saccharomyces cerevisiae* alpha-galactosidase (CAA85739) SEQ ID NO: 64

FAMILY 36 GenBank Accession Nos and Abbreviations:
   *Escherichia coli* Alpha-galactosidase (YP_001464379)-SEQ ID NO: 65; *Aspergillus niger* Alpha-alactosidase (XP_001393350) SEQ ID NO: 66; *Geobacillus thermodenitrificans* alpha-galactosidase (YP_001126185) SEQ ID NO: 67; *Pediococcus pentosaceus* alpha-galactosidase (YP_804050) SEQ ID NO: 68; *Bacillus halodurans* alpha-galactosidase (NP_243089) SEQ ID NO: 69

DESCRIPTION OF THE PREFERRED EMBODIMENTS

The present invention is of novel polynucleotide sequences, which encode novel alkaline-α-galactosidases and methods of using same. Specifically, the present invention can be used to produce recombinant alkaline-α-galactosidases and antibodies directed thereto, which can be used in the food and agricultural industry, particularly in determining the germination potential of seeds.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings described in the Examples section. The invention is capable of other embodiments or of being practiced or carried out in various ways. Also, it is to be understood that the phraseology and terminology employed herein is for the purpose of description and should not be regarded as limiting.

α-galactosidases catalyze the hydrolysis of the terminal linked α-galactose moiety from galactose-containing oligosaccharides. These enzymes have important applications in a variety of commercial processes, such as in exclusion of raffinose contamination from beet sugar crystallization, removal of stachyose- and raffinose-associated flatulence from soybean milk and seroconversion of type B-blood to type O-blood.

The use of acidic forms of α-galactosidases is limited in applications which are better effected under alkaline pH conditions, such as the process of seroconversion which when done under acidic conditions often results in cell-lysis.

Although numerous applications can be improved using eukaryotic α-galactosidases, which are more efficient at alkaline pH conditions, only few examples of such enzymes have been reported and their biochemical makeup remains elusive.

As described hereinunder and in the Examples section, which follows, the present invention provides polynucleotide sequences, which encode α-galactosidases that exhibit optimal activity at an alkaline pH range.

Despite the availability in the prior art of partial amino acid sequence data, attempts at cloning of alkaline α-galactosidases coding sequences have been unsuccecsful [World Pat. Application No: WO 005351]. As is further detailed hereinunder, the present inventors have uncovered that the partial amino acid sequence information provided by the prior art included sequence errors which have otherwise prevented use of such sequences in cloning of alkaline α-galactosidases coding sequences.

As is further described hereinunder and in the Examples section which follows, the alkaline α-galactosidases coding sequences of the present invention were recovered only following laborious and time consuming analysis of available amino acid sequence data and putative plant homologues.

Thus, according to one aspect of the present invention there is provided an isolated nucleic acid comprising a genomic, complementary or composite polynucleotide sequence encoding a polypeptide having an alkaline-α-galactosidase activity.

As used herein the phrase "alkaline-α-galactosidase activity" refers to the ability of an enzyme to hydrolyse terminal-linked α-galactose moieties from galactose-containing oligosaccharides under neutral to basic pH conditions (i.e., pH 7-14).

As used herein the phrase "complementary polynucleotide sequence" refers to sequences, which originally result from reverse transcription of messenger RNA using a reverse transcriptase or any other RNA dependent DNA polymerase. Such sequences can be subsequently amplified in vivo or in vitro using a DNA dependent DNA polymerase.

As used herein the phrase "genomic polynucleotide sequence" refers to sequences, which are derived from a chromosome and thus reflect a contiguous portion of a chromosome.

As used herein the phrase "composite polynucleotide sequence" refers to sequences, which are at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to one preferred embodiment of this aspect of the present invention the polynucleotide sequence encodes a polypeptide, which is at least 79%, at least 80%, at least 85%, at least 90%, at least 95% or more, say 95%-100% homologous (similar+identical acids) to SEQ ID NO: 6, as determined using the BestFit software of the Wisconsin sequence analysis package, utilizing the Smith and Waterman algorithm, where gap creation penalty equals 8 and gap extension penalty equals 2.

Preferably, the polypeptide according to this aspect of the present invention includes one or more sequences of amino acids, which are set forth in SEQ ID NOs: 4, 7, 8 and 45-48. These sequences are conserved among the seed imbibition protein (SIP) family (see FIG. 2) and may form the catalytic as well as substrate binding domains, as is further detailed in Example 6 of the Examples section.

According to a preferred embodiment of this aspect of the present invention the encoded polypeptide is as set forth in SEQ ID NO: 6 or an active portion thereof. As used herein the phrase "active portion" refers to a portion of the alkaline-α-galactosidase, which retains alkaline-α-galactosidase activity and/or substrate recognition.

Alternatively or additionally, the polynucleotide according to this aspect of the present invention is preferably hybridizable with SEQ ID NO: 5.

Hybridization for long nucleic acids (e.g., above 200 bp in length) is effected according to preferred embodiments of the present invention under stringent or moderate hybridization, wherein stringent hybridization is effected by a hybridization solution containing 10% dextrane sulfate, 1 M NaCl, 1% SDS and $5 \times 10^6$ cpm $^{32}$P labeled probe, at 65° C., with a final wash solution of 0.2×SSC and 0.1% SDS and final wash at 65° C. and whereas moderate hybridization is effected using a hybridization solution containing 10% dextrane sulfate, 1 M NaCl, 1% SDS and $5 \times 10^6$ cpm $^{32}$P labeled probe, at 65° C., with a final wash solution of 1×SSC and 0.1% SDS and final wash at 50° C.

Yet alternatively or additionally, the polynucleotide according to this aspect of the present invention is preferably at least 84%, at least 86%, at least 88%, at least 90%, at least 92%, at least 94% or more, say 95%-100%, identical to SEQ ID NO: 5 as determined using the BestFit software of the Wisconsin sequence analysis package, utilizing the Smith and Waterman algorithm, where gap weight equals 50, length weight equals 3, average match equals 10 and average mismatch equals −9.

According to preferred embodiments the polynucleotide according to this aspect of the present invention is as set forth in SEQ ID NO: 5 or an active portion thereof.

The full-length cDNA of alkaline-α-galactosidase I, also termed as AgaI includes an open reading frame of 2262 base pairs (bp) (SEQ ID NO: 5, FIG. 1a) which encodes a 753 amino acid long protein with a calculated molecular weight of 82.773 KDa and a pI of 5.71.

The recombinant enzyme is characterized by optimal activity at neutral to alkaline pH (7-8) at relatively narrow temperature range (i.e., 30-37° C.), together with a broader substrate specificity, as compared to previously reported alkaline α-galactosidases. The recombinant enzyme's substrates include tetrasaccharides (e.g., stachyose), trisaccharides (e.g., raffinose) as well as disaccharides (e.g., melibiose), with higher affinity towards long carbohydrates (see example 3 of the Examples section).

These characteristics, particularly the neutral to alkaline activity optimum, together with the broad substrate specificity and most importantly the high affinity for stachyose and raffinose, distinguish the polynucleotide sequences of the present invention from previously reported alkaline α-galactosidases.

These characteristics of the isolated polynucleotides of the present invention enable potential use in diverse commercial processes including as potent indicators of the seed germination process.

As is mentioned hereinabove, isolation of the coding sequence set forth in SEQ ID NO:5 was not straightforward An approach using previously published amino acid sequences (SEQ ID NOs: 1 and 2) of internal peptides derived from a previously purified C. melo alkaline-α-galactosidase [World Pat. Application No: WO 005351] was formulated, however PCR cloning using these primers failed to amplify the desired sequence. This suggested that these internal peptide sequences had either resulted from a contamination or were incorrectly sequenced and as such were unsuitable for recovery of the corresponding gene.

Following several rounds of primer design and PCR amplifications, degenerate primers (SEQ ID NOs: 12 and 13) encompassing a 17 amino acid long N-terminus peptide (SEQ ID NO: 3), resulted in a desired PCR product (SEQ ID NO: 14), which proved to be useful for further gene cloning. The discrepancy between the internal peptide sequences and the amino-terminal peptide sequence could be explained by differential peptide sequencing methods, which were used to generate the same (World Pat. Application No: WO 0005351).

To circumvent the lack of downstream nested sequence information, a search for possible homologues to the melon-alkaline-α-galactosidase was effected. Amino acid BLAST analysis of the 17 amino acid N-terminal sequence (SEQ ID NO: 3) to a limited *Arabidopsis* data base (NCBI) revealed homology to a previously uncharacterized gene from *A. thaliana* termed "seed imbibition protein-like" (GenBank Accession No: NP_175970). In this search, 11 out of the 17 amino acids in the sequence were identical (see FIG. 1b). The *Arabidopsis* gene has been described as "seed imbibition protein-like" based on its sequence homology to a cDNA sequence from 24 hour germinated barley embryos (GenBank Accession No: M77845). The barley gene was termed a "seed imbibition protein (SIP) but remained otherwise uncharacterized. As of today, the SIP family includes a number of genes from a variety of sources all of which remain biochemically uncharacterized.

Consequently, the working hypothesis was that the alkaline-α-galactosidase from melon, with its 11/17 homology to the *Arabidopsis* gene and 8/17 homology to the barley gene, shared conserved sequences with the SIP proteins.

Homology analysis of the SIP proteins indicated some highly conserved sequences (For example, SEQ ID Nos: 4, 7, 8 and 47-49), one of which (SEQ ID NO: 49) allowed for the designing of a downstream degenerate primer useful for PCR-cloning (SEQ ID NO: 15). Use of this downstream primer along with the above described upstream primer (SEQ ID NO: 16) resulted in a 720 bp product (SEQ ID NO: 17).

Recovery of full-length alkaline-α-galactosidase-I (Aga-I, SEQ ID NO: 5) was then effected using the procedure of rapid amplification of cDNA ends (RACE), which facilitates the cloning of full-length cDNA 5' and 3'-ends after partial cDNA sequencing (further described in Example 1 of the Examples section).

The coding sequence of the N-terminal purified enzyme (SEQ ID NO: 3) was compatible with the deduced amino acid sequence of Aga-I (SEQ ID NO: 6, see FIG. 1b).

Given the high degree of conservation between the alkaline-α-galactosidase family members (see FIG. 2), the conserved sequences described herein may be useful in isolating additional members of this family from other cell types (e.g., from other tissues) as well as from other plant families.

Thus according to another aspect of the present invention there is provided a method of identifying novel alkaline-α-galactosidase polynucleotide sequences.

The method according to this aspect of the present invention is effected by the following steps.

First, polynucleotide sequences which encode polypeptides including an amino acid sequence selected from the group consisting of SEQ ID Nos: 4, 7, 8 and 47-48 are identified. Such polynucleotide sequences are considered as putative genes encoding alkaline-α-galactosidases.

The polynucleotide sequences are expressed either in-vivo or in-vitro.

Expressed polynucleotide sequences, which exhibit α-galactosidase activity under alkaline pH conditions are identified as alkaline α-galactosidases and as such are selected and are further biochemically (e.g., temperature and substrate specificity, pH sensitivity, pI) and genetically (e.g., expression, phylogenetics, etc.) characterized (see Examples 3-5 of the Examples section).

Expressed polynucleotide sequences used as a potential source for identifying novel alkaline-α-galactosidases according to this aspect of the present invention are preferably libraries of expressed messenger RNA [i.e., expressed sequence tags (EST), cDNA clones, contigs, pre-mRNA, etc.] obtained from tissue or cell-line preparations which can include genomic and/or cDNA sequence.

Expressed polynucleotide sequences, according to this aspect of the present invention can be retrieved from preexisting publicly available databases (i.e., GenBank database maintained by the National Center for Biotechnology Information (NCBI), part of the National Library of Medicine, and the TIGR database maintained by The Institute for Genomic Research) or private databases (i.e., the LifeSeq.™ and PathoSeq.™ databases available from Incyte Pharmaceuticals, Inc. of Palo Alto, Calif.).

Alternatively, the expressed polynucleotide sequences utilized by the present invention can be obtained from sequence libraries (e,g, cDNA libraries, EST libraries, mRNA libraries and others). 15 It will be appreciated that such cDNA libraries can be constructed from RNA isolated from whole organisms, tissues, tissue sections, or cell populations.

Several methods of isolating the desired expressed polynucleotids sequences or polypeptide sequences encoded therefrom, include computer modeling, oligonucleotide hybridization techniques and immuno-methodologies. The predominant method would use areas of sequence conservation, either at the protein or nucleotide levels, and more specifically from within unique sequences such as SEQ ID NO: 4.

Computer modeling methods may be used to isolate expressed polynucleotide sequences. These methods include but are not limited to a number of molecular biology softwares including TFASTA, BLAST (Basic Local Alignment Search Tool, available through the NCBI website of the National Institutes of Health, USA), pairwise sequence alignment using either Bestfit (GCG Wisconsin Package) or MegAlign (DNASTAR, Inc.).

It may be appreciated that when a partial polynucleotide sequence is retrieved actions are taken to recover the full-length gene, such as by RACE technique. The retrieved polynucleotide may be used as a template for synthesizing the corresponding protein. Chemical synthesis techniques as well as recombinant techniques (either in a host cell system, or in a cell-free, in-vitro system) may be used to generate the same, and are further detailed hereinunder.

When using sequence libraries to select for the expressed polypeptides of this aspect of the present invention a variety of methods known to those of skill in the art may be used, such as those based on oligonucleotide hybridization (e.g., northern blot, southern blot, PCR amplification and the like or on protein-protein interactions.

For example, screening a cDNA library may be accomplished by inducing plated clones to express cloned exogenous sequences, transferring replicas of the induced plaques or colonies to filter membranes, and screening the membranes with an appropriate probe. According to this method, lifts of filters (for example, nylon or nitrocellulose) from an appropriately-induced cDNA library plates (induced by, for example, IPTG) are washed, blocked, and incubated with a selected probe for a period of time sufficient to allow the selected probe(s) to bind specifically to polypeptide fragments present on the filters. The filters may then be washed and reacted with a specific reagent, designed to recognize the polypeptides of the present invention (for example, antibodies directed to SEQ ID NO: 4). Additional reactions may be carried out as required to detect the presence of bound probe.

Once a clone is identified in a screen such as the one described above, it can be isolated or plaque purified and sequenced. The insert may then be used in other cloning reactions, for example, cloning into an expression vector that enables efficient production of recombinant fusion protein (further detailed hereinunder).

Expressed polypeptides, which are putative novel alkaline α-galactosidases, are examined for α-galactosidase activity at alkaline pH conditions, according to the protocol described by Smart and Pharr [Smart and Pharr (1980) Plant Physiol. 66:731-734 and Gao and Schaffer (1999) Plant Physiol. 119: 979-987].

Using the methodology described above, the present inventor has uncovered an additional member of the SIP/alkaline α-galactosidase family.

This novel alkaline α-galactosidase which is designated herein as Aga-II (SEQ ID NO:10) is encoded by SEQ ID NO: 9 and shares 58% identity at the DNA level and 59% homology at the amino acid level with Aga-I. Aga-II is a 772 amino acid long polypeptide, with a calculated molecular weight of 84.59 KDa and a pI of 5.71. Recombinant expression of this protein shows an intrinsic alkaline α-galactosidase activity similarly to that exhibited by Aga-I (see Example 3 of the Examples section).

Thus, the present invention encompasses polynucleotide sequences set forth in SEQ ID NOs: 5 or 9; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Since the polynucleotide sequence of Aga-II encodes a previously unidentified α-galactosidase protein, the present invention also provides a novel alkaline α-galactosidase protein, which is at least 82% identical to SEQ ID NO: 10 as determined using the BestFit software of the Wisconsin sequence analysis package, utilizing the Smith and Waterman algorithm, where the gap creation equals 8 and gap extension penalty equals 2 and functional homologues or portions thereof.

The polynucleotide and polypeptide sequences of the present invention may be used in a variety of commercial applications including seroconversion of group B erythrocytes to group O erythrocytes, modification of the rheological properties of an α-galactosyl saccharide containing plant gum, reduction of the capability of foodstuff to cause digestion associated flatulence and facilitation of crystallization of sugar beet sucrose from sugar beet molasses, as disclosed in World Pat. Appl. No: WO 005351, which is fully incorporated herein.

The availability of the isolated nucleic acids of the present invention allows the production of large amounts of purified forms of the encoded enzymes, which may be useful in the hereinabove described implementations.

The enzymes of the present invention can be produced by recombinant DNA techniques or chemical synthesis methods. However, recombinant expression of proteins is preferable due to the production of large amounts of protein at limited costs.

Thus, according to yet another aspect of the present invention there is provided a method of producing a recombinant alkaline α-galactosidase protein. The method is effected by several method steps, in which in a first step an expression construct, which includes any of the novel polynucleotides of the present invention positioned under the transcriptional control of a regulatory element, such as a promoter, is introduced into a cell.

In the next method step transformed cells are cultured under effective conditions, which allow the expression of the polypeptide encoded by the polynucleotide.

Lastly, the expressed polypeptide is recovered from the cell culture, and purification is effected according to the end use of the recombinant polypeptide.

Depending on the host/vector system utilized, any of a number of suitable transcription and translation elements including constitutive and inducible promoters, transcription enhancer elements, transcription terminators, and the like, can be used in the expression vector [see, e.g., Bitter et al., (1987) Methods in Enzymol. 153:516-544].

Other then containing the necessary elements for the transcription and translation of the inserted coding sequence, the expression construct of the present invention can also include sequences engineered to enhance stability, production, purification, yield or toxicity of the expressed polypeptide. For example, the expression of a fusion protein or a cleavable fusion protein comprising the alkaline α-galactosidase and a heterologous protein can be engineered. Such a fusion protein can be designed so that the fusion protein can be readily isolated by affinity chromatography; e.g., by immobilization on a column specific for the heterologous protein. Where a cleavage site is engineered between the alkaline α-galactosidase moiety and the heterologous protein, the alkaline α-galactosidase protein can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

A variety of prokaryotic or eukaryotic cells can be used as host-expression systems to express the alkaline α-galactosidase coding sequence. These include, but are not limited to, microorganisms, such as bacteria transformed with a recombinant bacteriophage DNA, plasmid DNA or cosmid DNA expression vector containing the alkaline α-galactosidase coding sequence; yeast transformed with recombinant yeast expression vectors containing the alkaline α-galactosidase coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the alkaline α-galactosidase coding sequence. Mammalian expression systems can also be used to express alkaline α-galactosidase. Bacterial systems are preferably used to produce recombinant alkaline α-galactosidase, according to the present invention, thereby enabling a high production volume at low cost.

In bacterial systems, a number of expression vectors can be advantageously selected depending upon the use intended for alkaline α-galactosidase expressed. For example, when large quantities of alkaline α-galactosidase are desired, vectors that direct the expression of high levels of protein product, possibly as a fusion with a hydrophobic signal sequence, which directs the expressed product into the periplasm of the bacteria or the culture medium where the protein product is readily purified may be desired. Certain fusion protein engineered with a specific cleavage site to aid in recovery of the alkaline α-galactosidase may also be desirable. Such vectors adaptable to such manipulation include, but are not limited to, the pET series of E. coli expression vectors [Studier et al. (1990) Methods in Enzymol. 185:60-89).

It will be appreciated that when codon usage for alkaline α-galactosidase gene cloned from C. melo is inappropriate for expression in E. coli, the host cells can be co-transformed with vectors that encode species of tRNA that are rare in E. coli but are frequently used by plants. For example, co-transfection of the gene dnaY, encoding tRNA.$_{ArgAGA/AGG}$, a rare species of tRNA in E. coli, can lead to high-level expression of heterologous genes in E. coli. [Brinkmann et al., Gene 85:109 (1989) and Kane, Curr. Opin. Biotechnol. 6:494 (1995)]. The dnaY gene can also be incorporated in the expression construct such as for example in the case of the pUBS vector (U.S. Pat. No. 6,270,0988).

In yeast, a number of vectors containing constitutive or inducible promoters can be used, as disclosed in U.S. Pat. No.

5,932,447. Alternatively, vectors can be used which promote integration of foreign DNA sequences into the yeast chromosome.

In cases where plant expression vectors are used, the expression of the alkaline α-galactosidase coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224: 838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems, which are well known in the art can also be used by the present invention.

In any case, alkaline α-galactosidase transformed cells are cultured under effective conditions, which allow for the expression of high amounts of recombinant alkaline α-galactosidase. Effective culture conditions include, but are not limited to, effective media, bioreactor, temperature, pH and oxygen conditions that permit protein production. An effective medium refers to any medium in which a cell is cultured to produce the recombinant alkaline α-galactosidase protein of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in Example 3 of the Examples section.

Depending on the vector and host system used for production, resultant proteins of the present invention may either remain within the recombinant cell; be secreted into the fermentation medium; be secreted into a space between two cellular membranes, such as the periplasmic space in E. coli; or be retained on the outer surface of a cell or viral membrane.

Following a certain time in culture, recovery of the recombinant protein is effected. The phrase "recovering the recombinant protein refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Proteins of the present invention are preferably retrieved in "substantially pure" form. As used herein, "substantially pure" refers to a purity that allows for the effective use of the protein in the diverse applications, described hereinabove.

Expression determination of the hereinabove described recombinant proteins can be effected using specific antibodies, which recognize the alkaline α-galactosidases of the present invention. Aside from their important usage in detection of expression of alkaline α-galactosidases, these antibodies can be used as to screen expression libraries and/or to recover desired proteins of the present invention from a mixture of proteins and other contaminants.

Thus, according to yet another aspect of the present invention there is provided an antibody or fragment thereof, which is specifically capable of binding the polypeptides of the present invention.

As used herein the term "antibody" includes a monoclonal and a polyclonal antibody, as well as functional fragments thereof, such as Fab, F(ab')$_2$, and Fv, which are capable of binding to macrophages. These functional antibody fragments are defined as follows: (i) Fab, the fragment which contains a monovalent antigen-binding fragment of an antibody molecule, can be produced by digestion of whole antibody with the enzyme papain to yield an intact light chain and a portion of one heavy chain; (ii) Fab', the fragment of an antibody molecule that can be obtained by treating whole antibody with pepsin, followed by reduction, to yield an intact light chain and a portion of the heavy chain; two Fab' fragments are obtained per antibody molecule; (iii) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (iv) Fv, defined as a genetically engineered fragment containing the variable region of the light chain and the variable region of the heavy chain expressed as two chains; and (v) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, N.Y., 1988, incorporated herein by reference).

Antibody fragments according to this aspect of the present invention can be prepared by proteolytic hydrolysis of the antibody or by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

The antibodies of the present invention can be used in numerous commercial applications and especially in determining the germination potential of seeds. Germination is the process in which the cells of the embryo change or mature from a state of dormancy to a state of intense metabolic activity, which is characterized by rapid metabolism of the RFO storage.

Determining the course of germination process in seeds has an important value in the assessment of seed quality. Quality is defined as the seed maturation stage, number and size of cracks in the seed envelope, germination percentage, speed of germination, uniformity of germination, vigour, percentage of normal seedlings, health and storability. Seeds with an optimal and uniform maturity and without cracks germinate more uniform and give less abnormal seedlings. Moreover, mature seeds have a better storability than less mature or immature seeds. Immature seeds and seeds with cracks are also more sensitive to infection by diseases. Furthermore, a negative health condition during the development of the seed can disturb the maturation process. This will result in unhealthy seeds with a lower degree of maturity than for healthy seeds.

Despite their immense importance, only very few examples for molecular markers which are indicative of the germination process are currently available, as disclosed in U.S. Pat. No: 6,080,956, which is fully incorporated herein.

The observation that imbibed seeds contain up-regulated alkaline α-galactosidase activity (see Example 4 of the Examples section), suggests that the enzymes of the present invention can serve as molecular indicators of the germination process.

Thus according to an additional aspect of the present invention there is provided a method of determining the germination potential of seeds.

The method is effected by analyzing the seeds for activity or expression level of the polypeptide of the present invention, which activity or expression levels are indicative of the germination potential of the seeds.

The expression levels of the polypeptides of the present invention, can be determined in seeds by conventional methods well known to those of skill in the art. For instance, the techniques of immunodetection are described in current protocols in immunology, Coligan et al., Eds., John Wiley & Sons, New York (1995).

In order to detect polypeptide-levels in seeds, crude extracts of the total and soluble proteins are attained; the seeds are crushed in a blander in the presence of liquid nitrogen. The powder is taken up in a homogenization buffer (Hepes pH 8), which contains various protease inhibitors (e.g., benzamidine-HCl, phenylmethylsulphonyl fluoride and the like) and the mixture is centrifuged to eliminate cell-debris. Extracted proteins can then be separated on polyacrylamide gel in the presence of SDS (SDS-PAGE) and immunoblotted. Alternatively, the activity of the polypeptides in the seed extracts can be measured using any α-galactosidase enzymatic assay available. Preferably used is the method described by Smart and Pharr [Plant Physiol. 66:731-734 (1980)], which is described in length in the Examples section.

mRNA levels of the polypeptides of the present invention may also be indicative of the germination process. mRNA levels can be determined by a variety of methods known to those of skill in the art, such as by hybridization to a specific oligonucleotide probe (e.g., Northern analysis).

Thus according to yet an additional aspect of the present invention there is provided an oligonucleotide of at least 17, at least 18, at least 19, at least 20, at least 22, at least 25, at least 30 or at least 40, bases specifically hybridizable with the polynucleotide sequences described hereinabove.

To specifically detect the polynucleotide sequences of the present invention, measures are taken to design specific oligonucleotide probes, which would not hybridize with other related genes under the hybridization conditions used. FIG. 2 illustrates conserved sequences, which may be useful for the design of specific oligonucleotides.

For example, for an oligonucleotide probe specifically hybridizable with Aga-I one may use the following oligonucleotide sequence: 5'-CAGATCGGTAGTCGC-CGAGTTTTT-3' (SEQ ID NO: 43). Alternatively, for specific detection of Aga-II the following oligonucleotide sequence may be used: 5'-AACAGTAAAAGTCTACATGTTTTC-3' (SEQ ID NO: 44).

Hybridization of short nucleic acids (below 200 bp in length, e.g. 17-40 bp in length) can be effected by the following hybridization protocols depending on the desired stringency; (i) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$; (ii) hybridization solution of 6×SSC and 0.1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$, final wash solution of 6×SSC, and final wash at 22° C.; (iii) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 37° C., final wash solution of 6×SSC and final wash at 22° C.

The oligonucleotides of the present invention can be used in any technique which is based on nucleotide hybridization including, subtractive hybridization, differential plaque hybridization, affinity chromatography, electrospray mass spectrometry, northern analysis, RT-PCR and the like. For PCR-based methods a pair of oligonucleotides is used.

Thus, according to further aspect of the present invention there is provided a pair of oligonucleotides each independently of at least 17, at least 18, at least 19, at least 20, at least 22, at least 25, at least 30 or at least 40 bases specifically hybridizable with the isolated nucleic acid described herein in an opposite orientation so as to direct exponential amplification of a portion thereof in a nucleic acid amplification reaction, such as a polymerase chain reaction. The polymerase chain reaction and other nucleic acid amplification reactions are well known in the art and require no further description herein. The pair of oligonucleotides according to this aspect of the present invention are preferably selected to have compatible melting temperatures (Tm), e.g., melting temperatures which differ by less than that 7° C., preferably less than 5° C., more preferably less than 4° C., most preferably less than 3° C., ideally between 3° C. and 0° C.

The discovery of the genes, which encode for the first step of galactosyl-saccharide metabolism sheds light on the initial stages of seed germination, and as such can be used as accurate indicators thereof.

It will be appreciated that other than the utility described above, the polynucleotide and polypeptide sequences of the present invention may also be used in the removal of RFOs from soy and other legume seed products, the modification of plant gum rheological properties, the hydrolysis of the raffinose contaminant in sugar beet molasses and the seroconversion of blood type B to the universal donor type O.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Procedures

Fruit material and chemicals—Melon (*Cucumis melo* L. cv C-8) plants were grown under standard conditions in a greenhouse in Bet-Dagan, Israel. Female flowers were hand-polinated and tagged at anthesis. Fruit load was limited to 1-fruit per plant following days after application (DAA). Primary fruits were harvested from after from 3 days prior to anthesis and throughout fruit development. Tissue were thinly sliced and immediately frozen in liquid nitrogen prior to storage at −80° C.

Unless otherwise indicated, chemicals and enzymes were purchased from Sigma (Sigma, Rehovot, Israel) and Boehringer Mannheim (Roche Diagnostics Corp.).

RNA isolation, cDNA synthesis and RACE—Total RNA from melon fruits of different developmental stages was extracted according to the protocol of "EZ-RNA" isolation kit [Biological Industries Co., Bet-Ha'emek (1990) LTD. Israel]. Briefly: cells were disrupted in guanidinium/detergent solution. Thereafter, RNA was purified by organic extraction and LiCl/alcohol precipitation. Purified RNA was further treated with RNase-free DNase for 30 minutes at 37° C. DNase was inactivated by adding EDTA to 5 mM final concentration and then phenol and chloroform extraction following by ethanol precipitation.

Total purified RNA was used as a template for first strand cDNA synthesis using the Superscript II reverse transcriptase (Gibco BRL. Life Technologies, UK). Sequences at the 5' and 3' ends of the cDNA were obtained using oligo-dT primers or RACE PCR [Frohman M A (1993) Methods Enzymol. 218: 340-356] using oligonucleotide primers obtained from Clontech, Palo Alto, Calif., USA. dNTPs were obtained from (Gibco BRL. Life Technologies, UK). Gene-specific oligonucleotide primers were obtained from MBC Israel.

DNA Constructs for Heterologous Expression of Aga-I and Aga-II in *E. coli*—The coding sequences of alkaline-α-galactosidase I and II (SEQ ID NOs: 5 and 9, respectively) were PCR amplified. Table 1 below lists oligonulceotide primers used for amplification reaction.

TABLE 1

| Gene | Orientation | Primer | SEQ ID NO: |
|---|---|---|---|
| Aga I | Sense | 5'- ATGACGGTTGGTGCTGGA ATTACTATCTCCGAT -3' | 39 |

TABLE 1-continued

| Gene | Orientation | Primer | SEQ ID NO: |
|------|-------------|--------|------------|
| Aga I | Antisense | 5'- TCATAGTTCAATTCTTAT ATCCCAAAGGTAGAAGTC -3' | 40 |
| Aga II | Sense | 5'- ATGACGGTCACACCGAAA ATTTCTGT -3' | 41 |
| Aga II | Antisense | 5'- GCCTCCACCATACACATT CATTGCTC -3' | 42 |

PCR reaction was effected as follows: Initial denaturation step at 94° C. for 1 min followed by 28 cycles of [94° C. for 15 s, 66° C. for 30 s, and 68° C. for 3 minutes].

PCR products were resolved on a 1% agarose gel. Bands of expected mobility were extracted and subcloned into the pGEM-T shuttle vector (Promega, Madison. Wis., USA).

Bacterial expression plasmid pIVE (Promega, Madison Wis., USA), encoding the entire recombinant Aga-I or Aga-II proteins with an additional N-terminal tag of histidine residues under the control of the T7 promoter, was constructed by Not I digestion.

Heterologous Expression of Aga I and Aga II in E. coli—E.coli BL21 (DE3) LysE cells [Dubendorff J W and Studier F W (1991) "Controlling basal expression in inducible T7 expression system by blocking the target T7 promoter with lac repressor" J. Mol. Biol. 219: 45-59] were co-transformed with pIVE-Aga-I or pIVE-Aga-II expression vectors along with a plasmid containing the dnaY gene coding for tRNA$^{Arg}_{AGA/AGG}$. The latter was added in the transformation mixture, as cellular enrichment with tRNA$^{Arg}_{AGA/AGG}$ by cotransfection with the dnaY gene, which supplies this minor tRNA, has been reported to result in high-level production of this rare codon with greatly improved cell viability and plasmid stability [Brinkmann U et al. (1989) Gene 85:109-14 and Wise A et al (1997) Plant Mol. Biol. 33:723-8].

Individual bacterial colonies were grown in 50 ml flasks containing 10 ml LB$^{Amp}$ medium until an optical density (OD, A$_{600}$) of 0.6 was reached. Induction of T7 RNA polymerase was initiated by addition of 0.4 mM IPTG. Cells were further grown to an OD of 1.5 (6 hours) and subsequently collected by centrifugation at 4,000 g (4° C., Sorvall centrifuge, rotor type GSA; Sorvall-Du Pont, Dreieich, Germany) for 10 minutes.

Sediments were resuspended in 2.5 ml extraction buffer including 20 mM phosphate buffer pH 8, 1 mM EDTA pH 8, 500 mM NaCl, 0.1% Ttriton-X-100, 2.5 mM Dtt and 1 mg/ml lysozyme. Cell-disruption was allowed to proceed for 1 hour at 4° C. while enforcing mechanical rupturing of cells using a cell and DNA disruptor nebulizer (Bioneb, Bloomington, Indiana University, USA). Crude soluble protein extracts were obtained after centrifugation at 15,000 g for 30 minutes at 4° C. and collection of the soluble fraction.

Purification of recombinant alkaline-α-galactosidase I and II proteins—Recombinant alkaline-α-galactosidases were purified from transformed E. coli crude protein extract by nickel resin affinity chromatography. Resin (Invitrogen, The Netherlands) was equilibrated by washing 5 times with washing buffer [50 mM NaH$_2$PO$_4$ pH 8, 300 mM NaCl and 20 mM imidazole]. Thereafter, 250 μl of washed resin was mixed with 250 μl of E. coli protein extract and incubated at 4° C. for 1 hour while agitating (200 RPM). Extract-treated resin was loaded on a column and washed 3 times with 1 ml washing buffer and then eluted 3 times with 50 mM NaH$_2$PO$_4$ pH 8, 300 mM NaCl and 250 mM imidazole. Fractions were collected and numbered.

Proteins dissolved in the fractions were precipitated by adding trichloroacetic acid (20% final concentration) and incubation on ice for 30 to 45 min, followed by sedimentation. Precipitates were washed with 500 μl of ice-cold acetone prior to SDS-PAGE to remove remaining trichloroacetic acid.

Gel electrophoresis—SDS-PAGE was carried out with a Mini-protean II apparatus (Bio-Rad) using 1 mm-thick slab gels containing 8% acrylamide according to the procedure of Laemmli [Laemmli UK (1970) Nature 227:680-685]. Gels were stained with Coomassie brilliant blue R-250 (Sigma) and destained in a methanol:acetic acid:water solution (3:1:6).

α-galactosidase assay of E. coli extracts—α-galactosidase activity was assayed as described by Smart and Pharr [Smart and Pharr (1980) Plant Physiol. 66:731-734] and as performed by Gao and Schaffer (1999) Plant Physiol. 119:979-987]. Reaction was initiated by adding 50 μl enzyme aliquot to 200 μl McIlvaine buffer (made by mixing stock solutions of 0.1M citric acid and 0.2M sodium hydrogen phosphate to achieve pH of 5.0 and 7.0 for the assay of acid and alkaline activity, respectively) and 50 μl substrate (final concentration, 5 mM for pNPG and 10 mM for the natural substrates). Optimum pH for galactosidase activity was determined using the following reaction buffers: McIlvaine buffer, over a pH range of 4 to 7, 100 mM Hepes buffer over a pH range of 7 to 8, or 50 mM Tris buffer over a pH range of 8 to 8.7. Substrates used were the synthetic substrates based on p-nitrophenol (pNP-sugars), including the pNPα-gal (Sigma) and the natural substrates stachyose, raffinose and melibiose. In addition, substrate concentration dependence of the reaction was measured by varying the substrate concentrations from 0-10 mM. $K_m$ and $V_{max}$ values were calculated using Lineweaver-Burk plots.

Extraction of a-galactosidase activity from barley embryso—20 barley seeds (var. Himalaya) were germinated on moist filter paper and kept at 25 C for 24 hrs. Embryos were surgically separated from the endosperm and the two tissues were separately extracted and assayed, using pNPα-Gal, as in Gao and Schaffer (1999). In parallel, dry seeds were assayed in the same manner. The effect of pH was studied by varying the McIlvaine buffer components, as above, to give pH values from 4.0 to 8.7.

Example 1

Cloning of Alkaline-α-galactosidase I Gene

The cloning strategy of alkaline-α-galactosidase I gene was based on the previously identified 17 amino acid sequence, which comprises the amino terminus end of alkaline-α-galactosidase I protein (SEQ ID NO: 3, World Pat. Appl. No: WO 005351). This sequence was found to be homologous to a previously reported family of genes termed seed imbibition like proteins (SIPs). Sequence analysis of the SIP family identified two conserved motifs, which together with the known 5' sequence of the gene allowed recovery of the full-length gene.

Cloning the 5' end sequence of the alkaline-α-galactosidase I gene—

Degenerate primers were designed for the PCR cloning of the 51 bp nucleotide sequence encoding the N-terminal sequence of alkaline-α-galactosidase I (SEQ ID NO: 14). Table 2 below lists the degenerate primers used.

TABLE 2

| Amino acid sequence | Orientation | Primer | SEQ ID NO. |
|---|---|---|---|
| TVGAGI | Sense | 5'-ACIGTBGGBGCBGGBATHAC-3' | 18 |
| TVGAGI | Sense | 5'-ACYGTNGGNGCNGGYAT-3' | 19 |
| TVGAGI | Sense | 5'-ACYGTNGGNGCNGGRAT-3' | 20 |
| TVGAGI | Sense | 5'-ACRGTNGGNGCNGGYAT-3' | 21 |
| TVGAGI | Sense | 5'-ACRGTNGGNGCNGGRAT-3' | 12 |
| NLTVLG | Antisense | 5'-NCCNAGIACIGTNAGRTT-3' | 22 |
| NLTVLG | Antisense | 5'-NCCYAAIACIGTNAGRTT-3' | 23 |
| NLTVLG | Antisense | 5'-NCCNAGIACIGTYAARTT-3' | 24 |
| NLTVLG | Antisense | 5'-NCCYAAIACIGTYAARTT-3' | 13 |

Table 2 Cont.

PCR was carried out in a final volume of 50 µl containing 200 pmol of each of the degenerate-oligonucleotide primers of Table 2, 1 ng of the cDNA template described hereinabove, and 1 µl of Thermo Stable Advantage 2 polymerase mix/DNA polymerase (Clontech, Palto Alto, Calif., USA). PCR amplification reactions were performed in an automated thermocycler (Mastercycler gradient, Eppendorf, Germany). Amplifications were carried out by an initial denaturation step at 94° C. for 1 min followed by 60 cycles of [94° C. for 15 s, 44° C. for 1 minute, and 72° C. for 10 s].

At the end of the PCR amplification, products were analyzed on agarose gels stained with ethidium bromide and visualized with UV light.

PCR reaction employing the degenerate primer pairs of SEQ ID NOs: 12 and 13 resulted in a single band, which corresponded to the molecular weight of the expected 51 bp product. This band was excised from the agarose gel using high pure PCR product purification kit, Roche, Germeny. Nucleotide sequencing confirmed that the resultant product (SEQ ID NO: 14) corresponded to the nucleotide sequence encoding the amino-terminus of alkaline-α-galactosidase I. This allowed the synthesis of a 25 bp sense primer (SEQ ID NO: 16), which constituted the 5' primer for gene cloning.

Internal primer design —Design of internal primers for PCR-mediated gene cloning was based on homology search. A BLAST analysis (Basic Local Alignment Search Tool, available through the NCBI website of the National Institutes of Health, USA), limited to the Arabidopsis genome effected on the 17 amino acid sequence of the N-terminus of alkaline-α-galactosidase I (SEQ ID NO: 3) showed homology (i.e., 11 out of the 17 amino acids were identical) with an uncharacterized gene from *Arabidopsis thaliana*, termed "seed imbibition protein (SIP)-like" (GenBank Accession number: NP_175970).

Cloning the alkaline-α-galactosidase I full-length gene—Amplification reaction using the above-described sense-oriented primer (SEQ ID NO: 16) and antisense downstream degenerate primer (SEQ ID NO: 15), enabled the cloning and sequencing of a 720 bp sequence (SEQ ID NO: 17). PCR was performed as follows: Initial denaturation step at 94° C. for 1 min followed by 45 cycles of [94° C. for 15 s, 50° C. for 1 minute, and 72° C. for 1 minute].

Following the cloning of the 720 bp segment the full-length gene was cloned using the RACE (Rapid Amplification of cDNA ends) technique. This was effected by 3'-Race (SMART RACE cDNA Amplification Kit, Clontech, Palo Alto, Calif., USA) using the following gene-specific primers: 5'-GTGGGTGCTGGATCAGATCCTT-3' (sense, SEQ ID NO: 25); 5'-ACCATTACTTATGCAGTCAAGTCTG-3' (sense-nested, SEQ ID NO: 26) and the antisense 3'-RACE cDNA synthesis oligonucleotide primer (Clontech, Palo Alto, Calif., USA).

Amplification reaction was effected as follows: Initial denaturation step at 94° C. for 1 min followed by 35 cycles of [94° C. for 30 s, 66° C. for 30 s, and 68° C. for 2 minutes].

RACE product sequencing (SEQ ID NO: 27) enabled full length cloning of alkaline α-galactosidase I. PCR reaction was effected using the following oligonucleotide primers: 5'-ATGACGGTTGGTGCTGGAATTACTATCTCCGAT-3' (sense, SEQ ID NO: 28) and 5'-TCATAGTTCAATTCT-TATATCCCAAAGGTAGAACTC-3' (antisense, SEQ ID NO: 29) and performed in the presence of 1.25 units of Ex taq polymerase (Takara Japan). PCR amplification included: Initial denaturation step at 94° C. for 1 min followed by 30 cycles of [94° C. for 15 s, 68° C. for 3 minutes].

Sequencing of the PCR race product revealed an open reading frame of 2262 bp, encoding the 754 amino acid long Aga-1 protein (FIG. 1a). The coding sequence of the N-terminal purified enzyme corresponded to the deduced amino acids of the cDNA sequence of alkaline-α-galactosidase I. The calculated molecular weight of 82.773 Kda was consistent with the approximate molecular weight of the native Aga-I protein [Gao Z and Schaffer AA (1999) Plant Physiol. 119:979-987].

Example 2

Cloning of Alkaline-α-galactosidase II Gene

Given the high degree of conservation between the alkaline-α-galactosidase family members, conserved sequences may be useful in isolating additional members of this family.

Experimental design and results—Degenerate oligonucleotide primers (SEQ ID NOs: 30 and 31) were designed and synthesized according to the conserved amino acid sequences: WWMTQR and WCTWDA (SEQ ID NOs: 32 and 33, respectively).

PCR was effected using Ex Taq polymerase (Takara Japan) under the following conditions: Initial denaturation step at 94° C. for 1 minute followed by 35 cycles of [94° C. for 30 s, 48° C. for 30 s, and 68° C. for 1 minute].

The resulting PCR product was sequenced (SEQ ID NO: 34). Oligonucleotide primers for 5' and 3' RACE were designed accordingly for the recovery of the full-length α-galactosidase II gene.

Gene-specific primers were used as follows: for 3' Race: 5'-GGA GAG CAA GGG TAA CGA TGG AG-3' (sense, SEQ ID NO: 35). PCR was effected as follows: Initial denaturation step at 94° C. for 1 minute followed by 45 cycles of [94° C. for 15 s, 66° C. for 1 minute and 68° C. for 3 minutes].

For 5' Race: 5'-ACGAGTAAGTGTAACCCTGCCACTG-3' (antisense, SEQ ID NO: 36). PCR was effected as follows: Initial denaturation step at 94° C. for 1 minute followed by 35 cycles of [94° C. for 30 s; 66° C. for 30 s and 68° C. for 2 minutes]. Full length alkaline α-galactosidase II cDNA was obtained by PCR using the following oligonucleotide primers: 5'-ATGACGGTCACACCGAAAATTTCTGT-3' (sense, SEQ ID NO: 37) and 5'-GCCTCCACCATACACATTCAT-TGCTC-3' (antisense, SEQ ID NO: 38). PCR was done as follows; Initial denaturation step at 94° C. for 1 minute followed by 28 cycles of: [94° C. for 15 s, 66° C. for 1 minute and 68° C. for 3 minutes]. PCR resulted in a single product of 2316 bp corresponding to the fill-length gene (SEQ ID NO: 9).

The full-length alkaline α-galactosidase II (Aga-II) gene has an open reading frame of 2319 bp, which encode 772 amino acids (84.593 KDa). Sequence comparison showed that Aga-I and Aga-II share 58% identity at the DNA level and 59% homology at the amino acid level. The alkaline α-galactosidases isolated according to the teachings of the present invention encode for proteins with identical calculated pI of 5.71.

Example 3

Enzymatic Characterization of Recombinant alkaline-α-galactosidase I and II

In order to establish that the cloned Aga-I and Aga-II genes encode for proteins with intrinsic alkaline α-galactosidase activity, the genes were functionally expressed and the protein products were biochemically characterized.

Results

As shown in FIG. 3, recombinant Aga-I and Aga-II proteins were highly expressed in *E. coli*, protease deficient cells. Protein purification on metal columns resulted in individual bands. As expected, the molecular weight of Aga-I was slightly lower than Aga-II, and both exhibited an approximate weight of 84 KDa. The molecular weight of Aga-I corresponded to the weight of the previously purified native alkaline-protein [Gao Z and Schaffer AA (1999) Plant Physiol. 119:979-987].

To ascertain that the cloned Aga genes of the present invention encode for alkaline-α-galactosidase, total protein extracts from Aga-I and Aga-II expressing cells were assayed.

Figure 4:
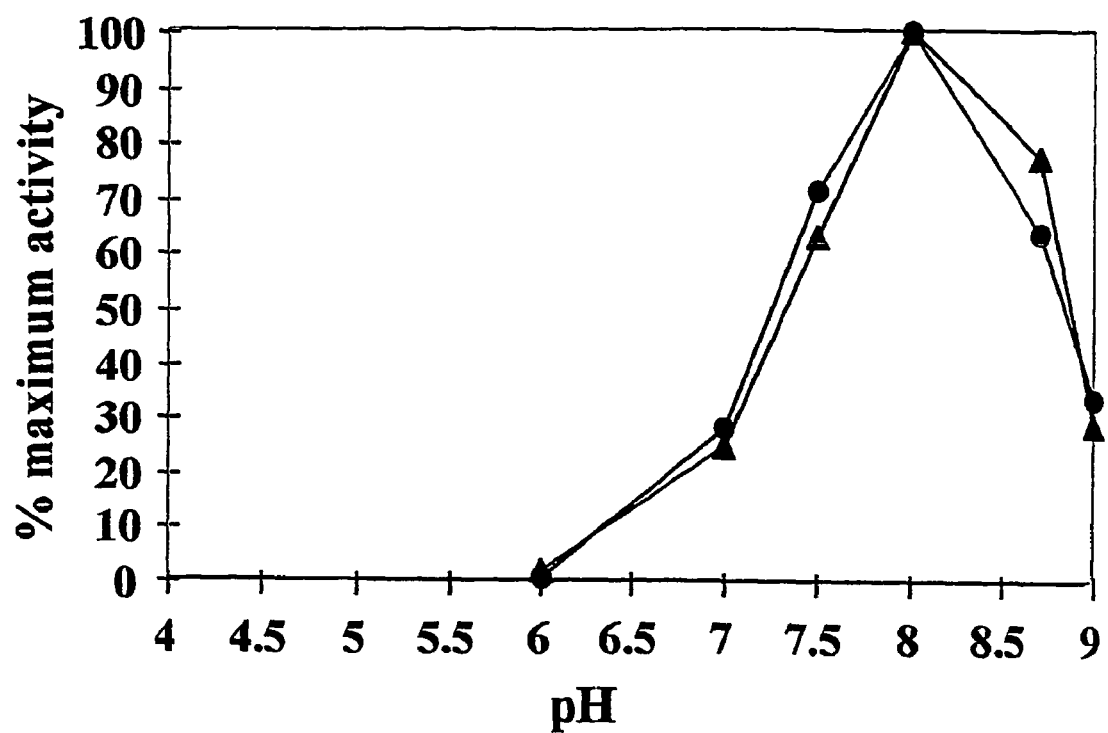
FIG. 4 shows alkaline-α-galactosidase activity of recombinant Aga-I and Aga-II. α-galactosidase activity of recombinant Aga-I (circles) and Aga-II (triangles) was examined in the indicated pH conditions and in the presence of 10 mM pNPG synthetic substrate. Activity is expressed as percentage of maximal activity as measured at 410 nm.

As shown in FIG. 4, enzymatic extracts from Aga-I and Aga-II-transformed *E. coli* exhibited an elevated α-galactosidase activity within a pH range of 7-9. Activity of both enzymes was maximal at pH 8. Control extracts (i.e., *E. coli* transformed with a control vector) exhibited no alkaline α-galactosidase enzymatic activity.

Recombinant Aga-I exhibited no activity with any of the following nitrophenyl substrates: pNP-αGlu, pNP-βGlu, pNP-αMan, pNP-βMan, pNP-Fuc and pNP-NacG. Although some activity towards pNP-βGal was observed in crude enzyme extract, this was mostly attributed to intrinsic bacterial activity, as non-transformed *E. coli* cells exhibited similar activity.

The substrate sensitivity of Aga-I together with the observation that non-transformed bacteria showed no α-galactosidase activity at pH 8 (data not shown), made it possible to perform remaining enzymatic characterization on total enzyme extract.

Recombinant Aga-I exhibited highest galactosidase activity in the neutral-alkaline pH range of 7.5-8, though activity was still observed at pH 9 (data not shown).

Aga-I activity was further limited to the temperature range of 30-37° C., and activity was significantly decreased above 40° C. (data not shown).

Substrate specificity analysis showed that recombinant Aga-I enzyme was able to hydrolyze stachyose, raffinose and melibiose at pH 8. Affinity constants (Km) and calculated specific activities are summarized in Table 3, below.

TABLE 3

| Substrate (10 mM) | Km (mM) | Activity (nmol/mg protein/minute) |
|---|---|---|
| Stachyose | 1.9 | 645 |
| Raffinose | 1.8 | 482 |
| Melibiose | 6 | 124 |

As is evident from Table 3, recombinant Aga-I exhibited significantly higher activity towards stachyose and raffinose than towards melibiose. The $K_m$ values indicate higher affinity of Aga-I towards stachyose and raffinose than towards melibiose.

The present results show that the cloned Aga-I and Aga-II genes of the present invention encode for proteins with an intrinsic alkaline-galactosidase activity. The two recombinant proteins exhibited maximum galactosidase activity at alkaline pH conditions. Molecular weight analysis, temperature sensitivity, substrate specificity and pI analysis show that recombinant Aga-I protein correspond to the partially purified protein, previously described by Gao and Schaffer [Gao Z and Schaffer A A (1999) Plant Physiol. 119:979-987].

Example 4

α-galactosidase Activity in Imbibed Barley Seeds

The alkaline-α-galactosidase genes of the present invention were cloned based on their high homology to the previously described seed-imbibition like proteins (SIP-like, see Examples 1 and 2). The first SIP was isolated from barley seeds, where high expression of SIP1 was found in the course of germination [Heck et al. (1991) Direct submission to gene bank M77845].

In order to determine whether alkaline-α-galactosidase activity is up-regulated during germination, enzymatic activity was assayed in imbibed barley seeds.

Results

To determine up-regulation of α-galactosidase activity during germination, dry and imbibed barley seed extracts were assayed in an acidic to alkaline pH range.

Figure 5:
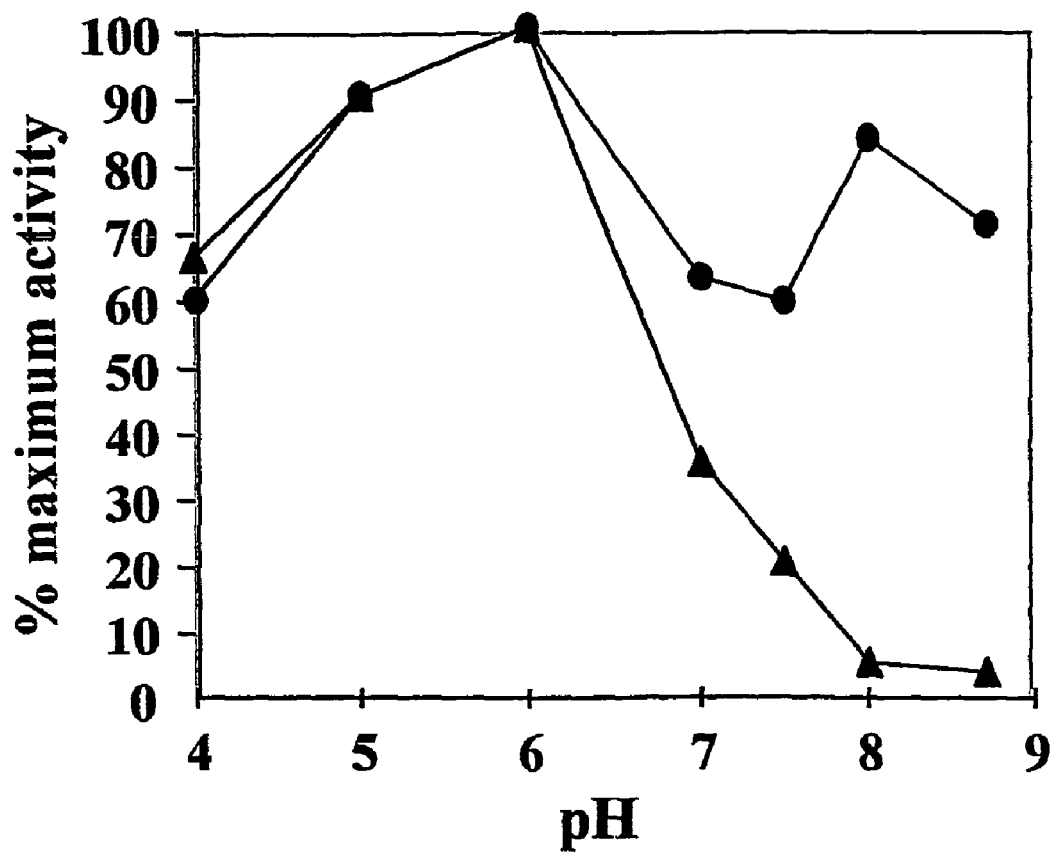
FIG. 5 shows alkaline α-galactosidase activity in imbibed barley embryos. Dry barley seeds were incubated in the dark for 24 hours at 20° C. Galactosidase activity in the indicated pH conditions was measured in seed-extracts prior to (triangles) or following (circles) imbibition.

As shown in FIG. 5, dry barley embryos and endosperm exhibited α-galactosidase activity only at acidic pH. Following 24 hours of imbibition at 20° C. the imbibed embryos also contained alkaline activity.

These results together with the high homology between alkaline-α-galactosidase gene and the prototypic SIP-1 (see FIGS. 2 and 6) identify the SIPs as alkaline α-galactosidases

Example 5

Figure 6:
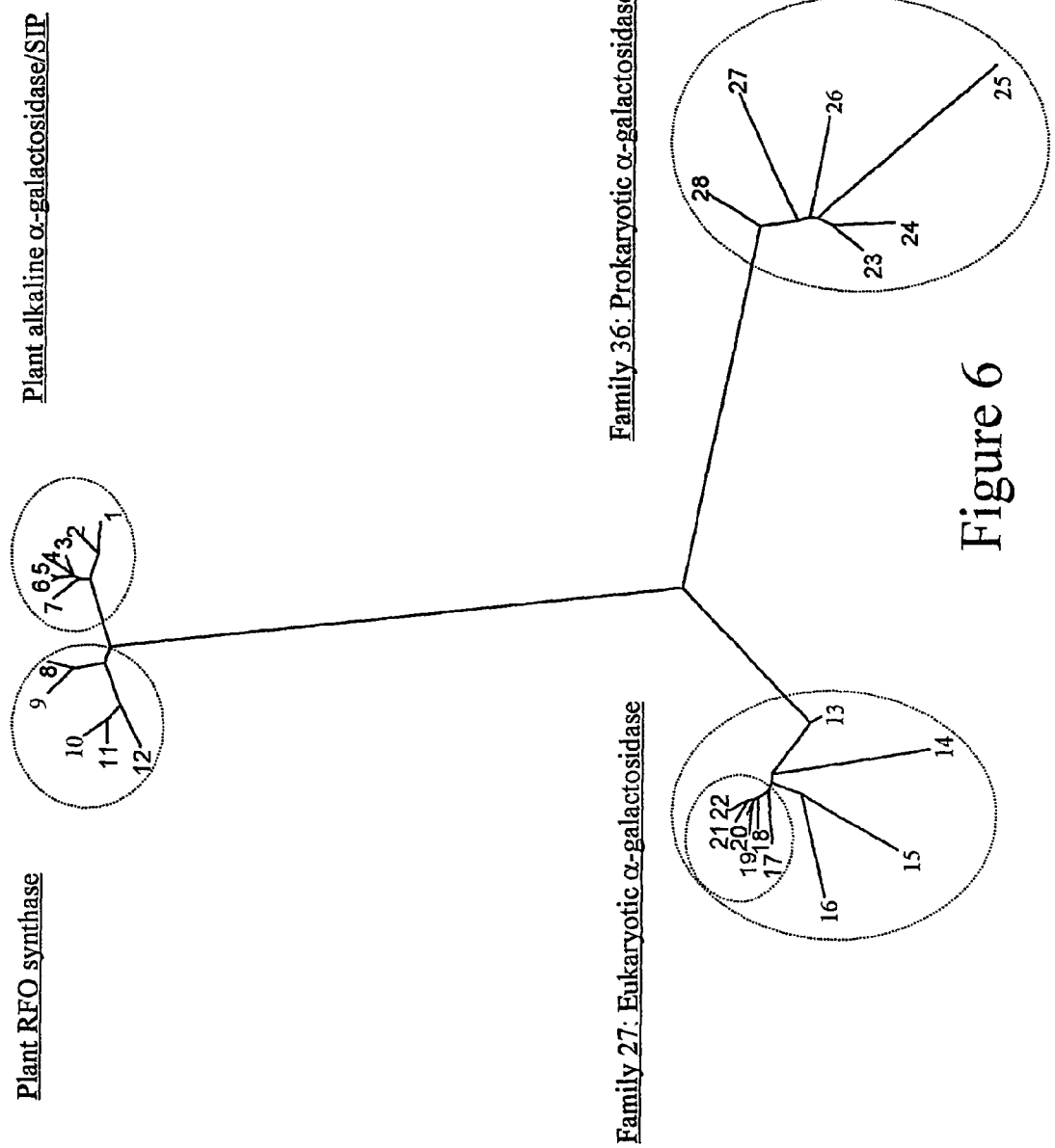
FIG. 6 illustrates a phylogenetic tree showing evolutionary relationship between alkaline α-galactosidases/SIPs, RFO synthases and eukaryotic and prokaryotic α-galactosidases. Analysis was done using the TREEview software (available from the Website of the University of Glascow, Zoology Department). Plant source, protein identity and accession numbers are indicated; 1-*Arabidopsis thaliana* NP_175970, 2-*Cucumis melo* α-galactosidase I, 3-*Cucumis melo* α-galactosidase II, 4-*Persea americana* CAB77245, 5-*Arabidopsis thaliana* CAB66109, 6-*Brassica oleraceae* x79330, 7-*Hordeum vulgare* S27762, 8-*Arabidopsis thaliana* BAB11595, 9-*Cucumis sativus* E15707, 10-*Pisum sativum* CAC38094, 11-*Vigna angularis* CAB64363, 12-*Arabidopsis thaliana* aad22659, 13-*Mortierella vinacea* BAA33931, 14-*Homo sapiens* P06280, 15-*Saccharomyces cerevisiae* P04824, 16-*Aspergillus niger* CAB46229, 17-*Arabidopsis thaliana* CAB87430, 18-*Arabidopsis thaliana* CAC08337, 19-*Lycopersicon esculentum* AAF04591, 20-*Coffea arabica* Q42656, 21-*Cyamopsis tetragonoloba* p14749, 22-*Glycine max* AAA73963, 23-*Bacillus stearothermophilus* AAD23585, 24-*Bacillus halodurans* BAB05947, 25-*Escherichia coli* P06720, 26-*Streptococcus mutans* P27756, 27-*Pediococcus pentosaceus* CAA76702.

Phylogenetic Analysis and Structural/Functional Predictions Pertaining to the SIP/alkaline α-galactosidase Family of Enzymes Phylogenetic analysis of the SIPs/alkaline α-galactosidase family identified according to the teachings of the present invention was effected using the TREEview software (available from the Website of the University of Glascow, Zoology Department, see FIG. 6).

Phylogenetic analysis of the SIPs/alkaline α-galactosidase family identified according to the teachings of the present invention was effected using the TREEview software (available from the Website of the University of Glascow, Zoology Department, see FIG. 6).

As shown in FIG. 6, phylogenetic data, thus obtained placed the alkaline α-galactosidases/SIPs in a cluster closely related to the group of RFO synthases but phylogenetically distinct from both the eukaryotic and prokaryotic α-galactosidases of families 27 and 36 of the glycosyl hydrolases (see the Background section). This suggests the alkaline α-galactosidase group identified according to the teachings of the present invention is plant specific, since no bacterial or non-plant eukaryotic genes were reported with significant homologies to this group. Interestingly, close relation between the α-galactosidases/SIPs of the present invention and the RFO synthases may be expected, as both the hydrolase and synthase/transferase reactions begin with the removal of a terminal glycosyl.

The phylogenetic analysis further revealed several critical regions as conserved sequences (see FIG. 7). Two conserved motifs DD(G/C)W and KxD were identified (SEQ ID NOs: 49 and 11, respectively) located in two distinct domains termed Box A and Box B, that span the three distinct groups of enzymes (see FIG. 7). Interestingly, within the DD(G/C)W sequence glycine and not cysteine appeared to characterize the newly identified alkaline galactosidases. Structural/functional studies of eukaryotic acid α-galactosidases suggested two carboxyl groups to constitute the α-galactosidase active site: one serving as the catalytic nucleophile and the other as the catalytic protonated general acid [Mathew CD and Balasubramaniam K (1987) Phytochemistry 26:1299-1300]. This was substantiated by the finding that the aspartic acid of the KxD sequence (SEQ ID NO: 11) serves as the catalytic nucleophile of the *Phanerochaete chrysosporium* enzyme [Hart DO et al. (2000) Biochemistry 39:9826-9836]. Since this motif is conserved between families it is likely that the proposed catalytic mechanism for the family 27 of enzymes can be extended to the other families as well. It is also possible that one of the aspartic acids in the conserved pair of the DDGW motif (SEQ ID NO: 49) functions as the acid/base catalyst. The limited number of interfamily conserved sequences containing aspartic acid or glutamic acid residues significantly narrows the possible candidates for the unknown catalytic carboxyl group.

The hydrophobic tryptophan adjacent to one of the carboxyl groups is proposed to maintain the protonated catalytic aspartic acid [Mathew CD and Balasubramanian K (1987) Phytochemistry 26:1299-1300]. Thus, the cross-family conservation of the aspartic acid of the DD(G/C)W, together with the conserved adjacent tryptophan, makes it a prime candidate for the catalytic function.

In addition to the conserved tryptophan immediately adjacent to the aspartic acid-aspartic acid pair of the DD(G/C)W motif, all the α-galactosidases also have at least one conserved tryptophan 30 to 34 amino acids upstream of the aspartic acid-aspartic acid (FIG. 7). Recently, this upstream tryptophan of coffee bean acid α-galactosidase (GenBank Accession No: Q42656) has been shown to be essential for activity and could functionally be replaced only by the aromatic amino acids, phenyl-alanine or tyrosine [Maranville E and Zhu A (2000) Eur. J. Biochem. 267:1495-1501]. This tryptophan may be juxtaposed in proximity to the catalytic aspartic acid contributing to the hydrophobic environment. Alternatively, the conserved tryptophan could function in hydrophopic substrate binding of the glycosyl oligosaccharides, as shown for α-glucosidase [Hrmova M et al. (1998) J. Biol. Chem. 273:11134-11143].

The results of the hereinabove described comprehensive sequence analysis present preliminary understanding of the catalytic and substrate recognition domains, and as such may be useful for the design of recombinant proteins and antibodies recognizing same.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

---

What is claimed is:

1. An isolated nucleic acid comprising a polynucleotide sequence encoding a polypeptide at least 95% homologous to SEQ ID NO: 6 with homology determined using the BestFit software of the Wisconsin sequence analysis package, utilizing the Smith and Waterman algorithm, where the gap creation equals 8 and gap extension penalty equals 2, wherein said polypeptide has alkaline α-galactosidase activity and wherein said polypeptide includes the amino acid sequence as set forth in SEQ ID NO: 4; and wherein said polypeptide is characterized by at least one tryptophan residue 30 to 34 amino acids upstream of the aspartic acid-aspartic acid residues of an aspartic acid-aspartic acid-(glycine/cysteine)-tryptophan motif.

2. The isolated nucleic acid of claim 1, wherein the polynucleotide is at least 95% identical to SEQ ID NO: 5, as determined using the BestFit software of the Wisconsin sequence analysis package, utilizing the Smith and Waterman algorithm, where gap weight equals 50, length weight equals 3, average match equals 10 and average mismatch equals −9.

3. The isolated nucleic acid of claim 1, wherein the polynucleotide sequence is as set forth in SEQ ID NO: 5 or a portion thereof encoding a polypeptide having alkaline α-galactosidase activity.

4. A nucleic acid construct comprising the isolated nucleic acid of claim 1.

5. An isolated host cell comprising the nucleic acid construct of claim 4.

6. An isolated nucleic acid encoding the polypeptide as set forth in SEQ ID NO: 6 or a portion thereof, wherein said polypeptide or portion thereof has alkaline α-galactosidase activity.

7. A nucleic acid construct comprising the isolated nucleic acid of claim 6.

8. An isolated host cell comprising the nucleic acid construct of claim 7.

9. A method of producing a recombinant alkaline α-galactosidase protein, which comprises: (a) introducing into a cell an expression construct encoding a polypeptide, wherein the polypeptide includes an amino acid sequence at least 95% identical to SEQ ID NO: 6 or a portion thereof having alkaline α-galactosidase activity and wherein the polypeptide includes the amino acid sequence as set forth in SEQ ID NO: 4; and wherein said polypeptide is characterized by at least one tryptophan residue 30 to 34 amino acids upstream of the aspartic acid-aspartic acid residues of an aspartic acid-aspartic acid-(glycine/cysteine)-tryptophan motif; (b) culturing the cell under effective conditions which allow expression of the polypeptide; and (c) recovering said polypeptide from the cell culture, thereby producing the recombinant alkaline α-galactosidase protein.

10. The isolated nucleic acid of claim 6, wherein said polynucleotide sequence is as set forth in SEQ ID NO: 5.

11. The method of claim 9, wherein said expression construct comprises the nucleic acid construct of an isolated nucleic acid encoding the polypeptide as set forth in SEQ ID NO: 6 or a portion thereof wherein said polypeptide or portion thereof has alkaline α-galactosidase activity.

* * * * *